United States Patent [19]

Haviv et al.

[11] 4,031,083

[45] June 21, 1977

[54] CEPHALOSPORIN ANTIBIOTICS

[75] Inventors: Fortuna Haviv, Montreal, Canada; Abraham Patchornik, Ness-Ziona; Janina Altman, Haifa, both of Israel

[73] Assignee: Yeda Research and Development Co., Ltd., Rehovot, Israel

[22] Filed: Oct. 24, 1975

[21] Appl. No.: 625,541

[52] U.S. Cl. .............................. 260/243 C; 424/246
[51] Int. Cl.$^2$ ............. C07D 501/22; C07D 501/32; C07D 501/30
[58] Field of Search ................................ 260/243 C

[56] References Cited

UNITED STATES PATENTS

| | | | |
|---|---|---|---|
| 3,341,531 | 9/1967 | Lewis et al. | 260/243 C |
| 3,865,820 | 2/1975 | Schorr et al. | 260/243 C |
| 3,919,206 | 11/1975 | Patchornik et al. | 260/243 C |
| 3,920,640 | 11/1975 | Schorr et al. | 260/243 C |

*Primary Examiner*—Donald G. Daus
*Assistant Examiner*—David E. Wheeler
*Attorney, Agent, or Firm*—L. R. Hattan; G. W. Rauchfuss, Jr.; E. O. Retter

[57] ABSTRACT

Novel cephalosporin antibiotic derivatives.

32 Claims, No Drawings

CEPHALOSPORIN ANTIBIOTICS

FIELD OF THE INVENTION

This invention relates to a novel cephalosporin derivatives useful as antibiotics and processes for the preparation.

SUMMARY OF THE INVENTION

Compounds of the following general Formula I are useful as antibiotic agents:

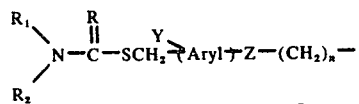
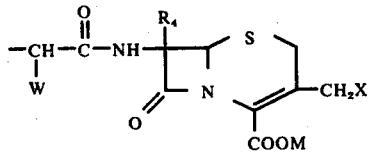

Formula I wherein each of $R_1$ and $R_2$ is selected from hydrogen and lower alkyl of from 1 to 4 carbon atoms or $-NR_1R_2$ taken together form a monocyclic heterocyclic group selected from pyrrolidino, piperidino and morpholino; R is oxygen or sulfur; Aryl is selected from phenyl and 2-thienyl; Y is selected from hydrogen, chlorine, bromine, a straight and branched lower alkyl group of from 1 to 4 carbon atoms and a lower alkoxy group of from 1 to 4 carbon atoms with the proviso that when Aryl is 2-thienyl, Y is hydrogen; Z is selected from a bond, oxygen, sulfur and imino with the proviso that when Aryl is 2-thienyl, Z is a bond; W is selected from hydrogen, methyl, amino, hydroxy, $SO_3H$, and $COOR_3$ wherein $R_3$ is selected from hydrogen and 5-indanyl; n is zero, 1 or 2 with the proviso that when W is other than hydrogen or methyl and Z is other than a bond, n is not zero; $R_4$ is selected from hydrogen and methoxy; M is selected from hydrogen; a pharmaceutically acceptable non-toxic cation; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen atom may be substituted with an alkyl group of from 2 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms and the amino nitrogen may be mono- or di-substituted with a lower alkyl group of from 1 to 4 carbon atoms; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio and 1,2,3-triazol-5-ylthio; and pharmaceutically acceptable salts thereof.

DETAILED DESCRIPTION OF INVENTION

It is apparent from the above formula I that the Aryl moiety is substituted with a thiocarbamatemethyl group which may be an aminothioxomethylthiomethyl group having the structure

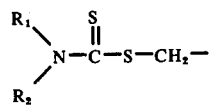

or may be an aminocarbonylthiomethyl group having the structure:

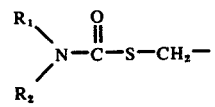

wherein $R_1$ and $R_2$ have the meanings defined in general Formula I. In general Formula I the substituent group as represented by M in addition to being hydrogen or a pharmaceutically acceptable non-toxic cation may also be alkanoyloxymethyl as represented by the structure:

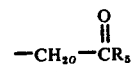

wherein $R_5$ is a straight or branched lower alkyl group of from 1 to 4 carbon atoms; alkanoylaminomethyl or alkoxycarbonylaminomethyl as represented by the structure

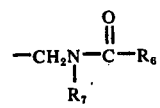

wherein $R_6$ is selected from a straight or branched lower alkyl group of from 1 to 4 carbon atoms and a straight or branched alkoxy group of from 1 to 4 carbon atoms and $R_7$ is selected from hydrogen and a lower alkyl group of from 1 to 4 carbon atoms; p-(alkanoyloxy)benzyl as represented by the structure

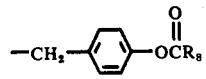

wherein $R_8$ is a straight or branched lower alkyl of from 1 to 4 carbon atoms, and aminoalkanoyloxymethyl as represented by the group

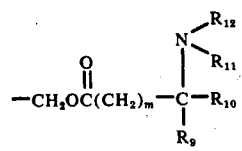

wherein m is 0 to 5, each of $R_9$ and $R_{10}$ is selected from hydrogen and lower alkyl of from 1 to 4 carbon atoms, and each of $R_{11}$ and $R_{12}$ is selected from hydrogen and a straight or branched lower alkyl group of from 1 to 4 carbon atoms.

Illustrative examples of straight or branched lower alkyl groups of from 1 to 4 carbon atoms which Y, $R_5$, $R_6$, $R_8$, $R_{11}$ and $R_{12}$ may represent are methyl, ethyl, n-propyl, isopropyl, n-butyl and tert-butyl.

Examples of lower alkyl groups of from 1 to 4 carbon atoms which $R_1$, $R_2$, $R_7$, $R_9$ and $R_{10}$ may represent are methyl, ethyl n-propyl and n-butyl.

Illustrative examples of straight or branched lower alkoxy groups which $R_6$ may represent are methoxy, ethoxy, n-propoxy, isopropoxy, sec-butoxy and n-butoxy.

In general Formula I, the substituent group X may represent in addition to hydrogen and acetoxy, a heterocyclicthio group selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio or 1,2,3-triazol-5-ylthio as represented by the following respective structures

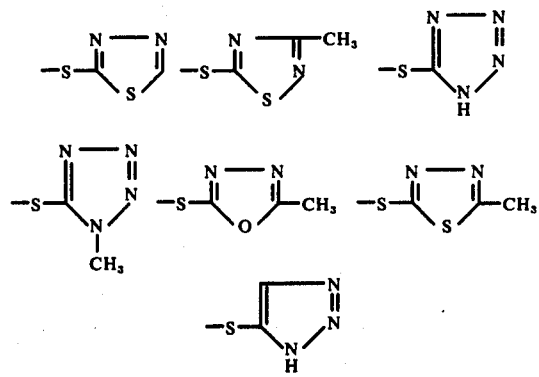

When the Aryl group in the compounds of general Formula I represent phenyl, each of the thiocarbamatemethyl substituent and the Y substituent may be individually attached to any of the positions 2 through 6 of the phenyl ring. Compounds of this type may be represented by the following general Formula II.

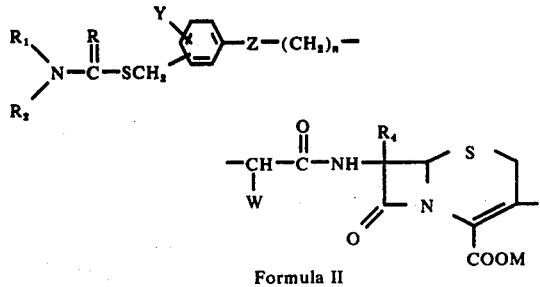

Formula II

The preferred positions of the attachments of the thiocarbamatemethyl substituent in the above Formula II are the ortho- and para-positions of the phenyl ring. In the above Formula II, the substituents as represented by R, $R_1$, $R_2$, Y, Z n, W, $R_4$, M and X have the meanings defined in general Formula I.

When the Aryl group in the compounds of general Formula I represent 2-thienyl, Y is hydrogen, and Z is a bond. Compounds of this type may be represented by the following Formula III.

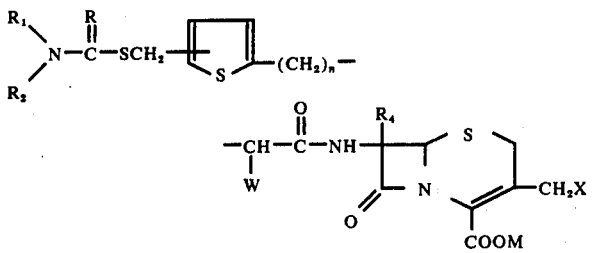

-continued
Formula III

In compounds of the above Formula III, the thiocarbamatemethyl substituent may be attached at the 4- or 5-positions of the thienyl group. In the above Formula III, the substituents as represented by R, $R_1$, $R_2$, n, W, $R_4$, M and X have the meanings defined in general Formula I.

In the compounds of general Formulas I to III, it is apparent that the $R_4$ substituent may be either cis or trans to the hydrogen atom at the 6-position of the cephalosporin derivatives. The compounds of Formulas I to III wherein the $R_4$ substituent is cis to the aforementioned hydrogen atom are preferred. Other preferred embodiments of this invention are:

A. compounds wherein W represents hydrogen, hydroxy, amino, $SO_3H$, and $COOR_3$ wherein $R_3$ represents hydrogen in that such substitution results in compounds having broader spectrum activity and/or improved oral activity for example wherein:
1. W represents hydroxy are more resistant to β-lactamase organisms;
2. W represents $SO_3H$ or $COOR_3$ wherein $R_3$ represents hydrogen have broader gram negative spectrum;
3. W represents $NH_2$ have improved oral activity;

B. compounds wherein $R_4$ represents methoxy are of particular interest in that such compounds demonstrate antibacterial activity against cephalosporinase producing gram negative organisms.

C. compounds wherein X represents acetoxy, 2-methyl-1,3,4-thiadiazol-5-ylthio, or 1-methyltetrazol-5-ylthio. Of the preferred embodiments set forth in (A), (B) and C. compounds wherein Z represents a bond are more preferred. The most preferred compounds of this invention are those represented by the following Formula IV

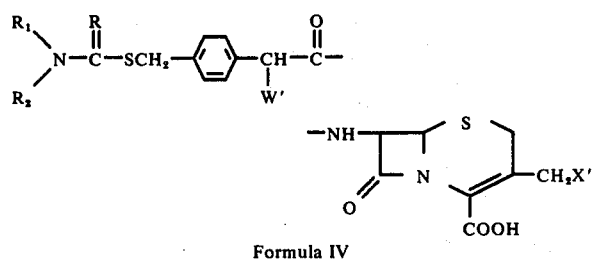

Formula IV wherein R, $R_1$ and $R_2$ have the meanings defined in general Formula I; W' is selected from hydrogen, hydroxy, amino, COOH or $SO_3H$; X' is selected from hydrogen, acetoxy, 2-methyl-1,3,4-thiadiazol-5-ylthio or 1-methyltetrazol-5-ylthio; and pharmaceutically acceptable salts thereof.

In the above Formula IV, compounds wherein the hydrogen atoms at the 6- and 7-positions are cis to one another are preferred.

The individual optical isomers of the compounds of this invention wherein W or W' is other than hydrogen are also included within the scope of this invention.

The non-toxic acid addition salts of the compound of this invention such as mineral acid addition salts, for example, hydrogen chloride, hydrogen bromide, hydrogen iodide, sulfates, sulfamate, and phosphate, an organic acid addition salt, for example, maleate, acetate, citrate, oxalate, succinate, benzoate, tartrate, fumarate, malate, mandelate, and ascorbate, are also included within the scope of this invention.

Also within the scope of this invention are the non-toxic pharmaceutically acceptable salts of the compounds of this invention wherein W represents COOH or $SO_3H$ and compounds wherein M represents hydrogen. Illustrative pharmaceutically acceptable salts of these acid derivatives are primary, secondary and tertiary amines, for example, cyclohexylamine, ethylamine and pyridine.

The pharmaceutically acceptable cations which may be present as the group M in the compounds of general Formulas I to III include alkali metal ions, for example, sodium ion, potassium ion, calcium ion as well as ammonium, and organic amine cations, for example, lower alkyl ammonium groups, such as triethylammonium and N-ethylpiperidine.

The salt forms of compounds of Formulas I to III wherein M is a pharmaceuticaly acceptable cation are prepared in the manner recognized in the art and may be formed in situ or by reacting the corresponding acid with base, for example, sodium bicarbonate or triethylamine.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds, and mammals, for example, cats, dogs, cows, sheep and horses, and humans. For oral administration, the compounds may be administered in the form of tablets, capsules, or pills or in the form of elixirs or suspensions. For parenteral administration, they are best used in the form of a sterile aqueous solution which may contain other solutes, for example, enough saline or glucose too make the solution isotonic. For topical administration, the compounds may be incorporated in creams or ointments Illustrative examples of bacterial against which the compounds of this invention are active are *Staphylococcus aureus*, *Salmonella schottmuelleri*, *Klebsiella pneumoniae*, *Diplococcus pneumoniae*, and *Streptococcus pyogenes*.

An illustrative example of a cephalosporin derivative of this invention is 3-[(acetyloxy)methyl]-7--[[2-[4-[[(aminothioxomethyl)thio]methyl]phenyl]acetyl]amino]-8-oxo-5-thia-1-azabicyclo[4.2.0]oct-2-ene-2-carboxylic acid. Additional examples of compounds of this invention are set forth hereinbelow in the specific examples which are representative of the invention.

The compounds of this invention wherein $R_3$ is hydrogen are prepared by coupling 7-aminocephalosporanic acid or a derivative of the formula

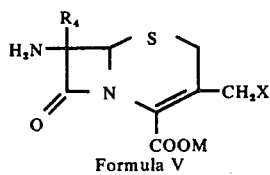

Formula V wherein $R_4$, M and X have the meanings defined in general Formula I with an acid of the following Formula VI or a function derivative thereof:

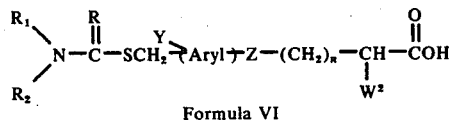

Formula VI wherein R, $R_1$, $R_2$, Aryl, Y, Z and n have the meanings defined in general Formula I, and $W^2$ is selected from hydrogen, methyl, amino, hydroxy, $SO_3H$ and COOH. When the substituent group $W^2$ in the above Formula VI represents an amino group, suitable blocking groups, for example, an acid salt such as hydrochloride salt, an acyl group, or tert-butoxycarbonyl may be employed to protect the amino function. Such blocking groups are removed after the coupling reaction by methods generally known in the art, for example, as described by Lemieux et al., in U.S. Pat. No. 3,657,232.

Functional equivalents of the acids as represented by Formula VI include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester for example, with p-nitrophenol, 2,4-dinitrophenol or thioacetic acid, may be used or the free acid as represented by Formula VI may be coupled with the 7-aminocephalosporanic acid derivative as represented by Formula V after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide. A preferred procedure is to use an acid anhydride for example an anhydride formed with pivalic acid.

The coupling reaction is generally carried out in the presence of a solvent. Suitable solvents include ethyl acetate, acetone, dioxane, acetonitrile, chloroform, ethylene chloride, tetrahydrofuran and dimethylformamide. As hydrophilic solvents are employed mixtures of these solvents with water are also suitable for the above reaction. The coupling reaction is generally carried out in the presence of a base, for example, an alkaline bicarbonate. The temperature of the reaction may vary from −10° to 100° C, and the reaction time may vary from about one-half hour to 10 hours. Higher yields of product are obtained when an anhydrous solution of a compound of Formula V is used. The cephalosporin products are isolated by conventional methods.

Compounds of Formula V wherein $R_4$ is hydrogen, M is hydrogen, or a pharmaceutically acceptable non-toxic cation, and X is hydrogen or acetoxy are commercially available or may be prepared by methods well-known in the art. The corresponding compounds wherein $R_4$ is methoxy may be prepared by the general procedures described in U.S. Pat. No. 3,778,432.

Compounds of Formula V wherein M is alkanoyloxymethyl may be prepared by reacting the corresponding acid in the form of a salt, such as, alkali metal salt or the triethylammonium salt with a compound of the formula

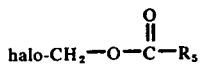

wherein halo is chlorine or bromine, and R₅ is a straight or branched lower alkyl group of from 1 to 4 carbon atoms by the general procedure described in U.S. Pat. No. 3,655,658.

Compounds of Formula V wherein M is alkanoylaminomethyl or alkoxycarbonylaminomethyl are prepared by treating the sodium salt of acid derivatives of Formula V in an organic solvent such as dimethylformamide or hexamethylphosphoramide, at room temperature with an equivalent amount of an alkanoylaminomethyl halide or an alkoxycarbonylaminomethyl halide for one-half to 3 hours after which the mixture is poured into ice water. The resulting precipitated product is isolated by standard procedures.

Compounds of Formula V wherein M is p-(alkanoyloxy)benzyl are prepared by adding two equivalents of the p-(alkanoyloxy)benzyl alcohol to a suspension of the sodium salt of acid derivatives of Formula V in dimethylformamide or hexamethylphosphoramide after which the mixture is cooled to 0° C, and 1.2 equivalents of dicyclohexylcarbodiimide and dimethylformamide are added dropwise to the mixture with stirring. The mixture is stirred at 0° C for one-half to 3 hours and then an additional 2 to 5 hours at room temperature. The formed dicyclohexylurea is removed by filtration and the filtrate is diluted with chloroform, methylene chloride or ethylacetate, washed with water and dried to give the product.

Compounds of Formula V wherein M is aminoalkanoyloxymethyl are prepared by mixing a suspension of the sodium salt of an acid of Formula V and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds of Formula V where X is a heterocyclicthio group as described in Formula I are prepared by dissolving 1 equivalent of the acid in the form of a salt, such as, the sodium salt wherein X is acetoxy in about 500 to 200 ml of water at a temperature of from 50° to C c under a nitrogen atmosphere and subsequently adding 1 equivalent of a base, such as, triethylammonium or sodium bicarbonate and 1 to 3 equivalents of an appropriate heterocyclicthio selected from a compound having the following structures

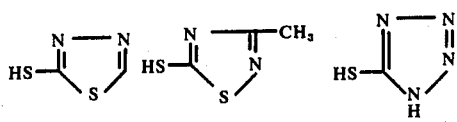

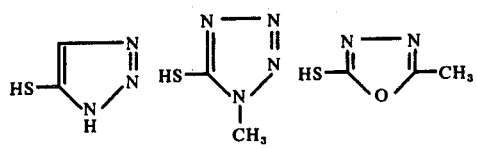

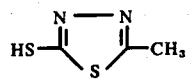

Compounds of general Formula VI are prepared by treating a compound of the following formula:

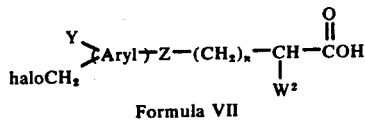

Formula VII wherein halo is chlorine or bromine, and Aryl, Y, Z, n and W² have the meanings defined in general Formula VI with a salt of thio- or dithiocarbamate having the formula

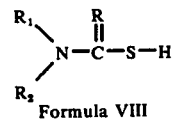

Formula VIII wherein R₁ and R₂ are selected from hydrogen and lower alkyl of from 1 to 4 carbon atoms and R is selected from oxygen and sulfur in a solvent, such as, a lower alcohol, for example, methanol, ethanol, isopropyl alcohol or n-butanol, or dimethylsulfoxide, dimethylformamide or aqueous mixtures of these solvents, for from 1/2 hour to 24 hours at a temperature range from 0° to 125° C. The products can be isolated by conventional procedures. In some instances it may be more convenient to convert the acid as represented by Formula VII to the corresponding methyl ester by, for example, treating the acid with diazomethane at −10° C then stirring the mixture for about 10 to 30 minutes at room temperature. Suitable salts of the compounds of Formula VIII include metal salts of Group IA, for example, sodium and potassium salts, amine and dialkylamine salts, for example, dimethylamine and diethylamine, pyrrolidine, piperidine and morpholine salts.

When the substituent group W² in compounds of general Formula VII represents amino, the amino group is protected by a suitable blocking group, for example, tert-butoxycarbonyl prior to the treatment with the carbamate salt of Formula VIII. The blocking group may be removed after the coupling reaction by a mild acid hydrolysis or hydrogenolysis by procedures known in the art.

Compounds of general Formula VIII are commercially available and known in the art or can be prepared by the procedures described by E. Emmet Reid, *Organic Chemistry of Bi-Valent Sulfur*, Chemical Publishing Co., New York, 1962, Vol. IV, p. 196 and by J. Parrod, Compt. rend, 234, 1062(1952).

The compounds of Formula VII are prepared by direct halomethylation as described hereinabelow of an acid of the formula:

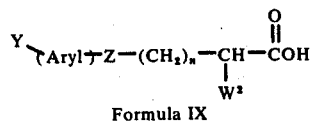

Formula IX wherein Aryl, Y, Z, $n$ and $W^2$ have the meanings defined in general Formula VI. The compounds of Formula IX are commercially available or are obtained by methods well-known in the art.

When the substituent group $W^2$ in the compounds of Formula IX represents amino, the amino group is protected by a suitable blocking group as for example described hereinabove in reference to compounds of general Formula VII.

The halomethylated derivatives of the compounds of Formula IX are obtained by several methods. For example, a compound of Formula IX with a source of formaldehyde such as paraformaldehyde, $ClCH_2OCH_3$, or formalin solution, in the presence of a Lewis acid, such as $ZnCl_2$, $AlCl_3$, $SnCl_4$ or $ClSO_3H$ in a solvent, such as, petroleum ether, chloroform, carbon tetrachloride or benzene at a temperature ranging from $-10°$ to $100°$ C during which time hydrogen chloride gas or hydrogen bromide gas is bubbled into the reaction mixture, will give compounds of general Formula VII.

The reaction of an aciid of Formula IX with 34-38% formalin in concentrated hydrochloric acid at temperatures ranging from $-10°$ to $100°$ C during which time hydrogen chloride gas or hydrogen bromide gas is bubbled through the reaction mixture also yields compounds of general Formula VII.

Additionally, upon reaction of an acid of Formula IX with trioxane in acetic acid or phosphoric acid at temperatures of from $-10°$ to $100°$ C during which time hydrogen bromide or hydrogen chloride gas is bubbled through the reaction mixture, compounds of general Formula VII are obtained. Or, the reaction of an acid of Formula IX in the presence of a Lewis acid, such as, those described hereinabove, with chloromethyl ether at temperatures of from $-10°$ to $100°$ C or the reaction of the acid in acetic acid or concentrated sulfuric acid with dichloromethyl ether in the presence of zinc chloride will give compounds of general Formula VII.

The compounds of Formula VII wherein $W^2$ represents COOH, and Aryl is phenyl are preferably obtained by treating the corresponding diethyl ester of Formula IX with 40% formalin in the presence of anhydrous zinc chloride in benzene at about $50°$ C during which time hydrogen chloride or hydrogen bromide gas is bubbled into the reaction mixture followed by acid hydrolysis.

Compounds of Formula VII wherein $W^2$ represents $SO_3H$ may be obtained by the halomethylation reactions described above using an acid of Formula IX wherein $W^2$ represents $SO_3H$ or the carboxymethyl ester thereof in which latter case the resulting halomethylated compound is converted to the free COOH by acid hydrolysis.

In the halomethylation of compounds of Formula IX wherein $W^2$ represents OH it may be advantageous to protect the OH group prior to halomethylation as described by V. Reichert, et al., Pharmazie 5, 10(1950).

Compounds of this invention wherein $R_3$ in 5-indanyl are prepared by reacting the corresponding acid, that is, compounds of general Formula I wherein $R_3$ is hydrogen with 5-indanol in an inert solvent in the presence of N,N'-dicylohexylcarbodiimide lat a pH of about 2.5 and a temperature of from $20°$ to $30°$ C. Equimolar amounts of the reactants are employed or a slight excess of the 5-indanyl may be used. The molar amount of N,N'-dicyclohexylcarbodiimide employed is equivalent to the molar amount of 5-indanol. Suitable solvents for the reaction are dioxane, tetrahydrofuran, ethyl acetate, dimethylformamide and methylene chloride.

The compounds of this invention may also be prepared by combining a modified polystyrene containing nitrophenol or hydroxysuccinimide groups with an acid of general Formula VI by the general procedure described in Canadian Pat. No. 892,580 issued Feb. 8, 1972, by substituting a compound of general Formula V for the penicillanic acid derivatives described therein.

Additionally, the compounds of this invention wherein X represents a heterocyclicthio group selected from 1,3,4-thiadiazol-5-ylthio, 3-methyl-1,2,3-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio or 1,2,3-triazol-5-ylthio and M represents hydrogen may be prepared by reacting the 3-[(acetyloxy)methyl]-derivative with the appropriate heterocyclicthiol group as represented by the following:

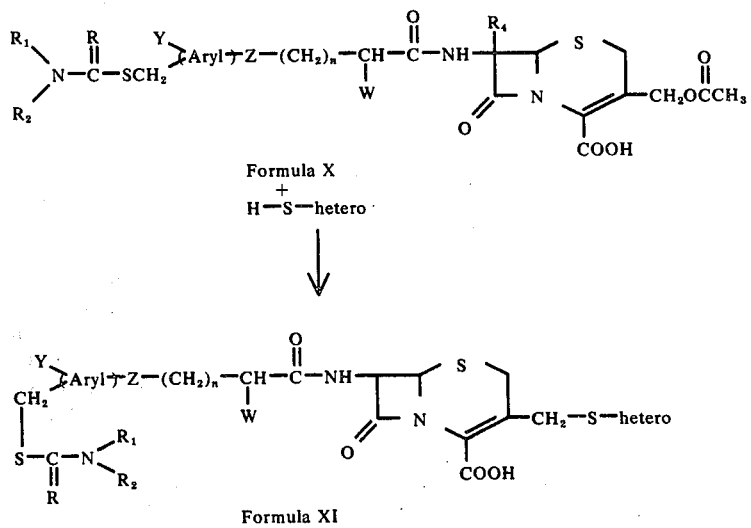

Formula X
+
H—S—hetero

↓

Formula XI

In the above Formula X and XI the substituent groups R, $R_1$, $R_2$, Aryl, Y, Z, $n$, W and $R_4$ have the meanings defined in general Formula I, and the moiety S-hetero is selected from 1,3,4-thiadiazol-5-ylthio, 3-methyl-1,2,4-thiadiazol-5-yl-thio, tetrazol-5-ylthio, 1-methyltetrazol-5-ylthio, 2-methyl-1,3,4-oxadiazol-5-ylthio, 2-methyl-1,3,4-thiadiazol-5-ylthio, or 1,3,4-triazol-5-ylthio.

In this reaction one equivalent of the sodium salt of Formula X is dissolved in water at a temperature of from 25° to 90° C under a nitrogen atmosphere followed by the addition of 1 equivalent of a base such as triethylamine or sodium bicarbonate and from 1 to 3 equivalents of the heterothiol derivative ater which the reaction mixture is stirred for about 2 to 6 hours at a temperature of from 25° to 90° C.

Compounds of this invention wherein M represents alkanoylaminomethyl or alkoxycarbonylaminomethyl, and W is other than COOH may also be prepared by reacting the corresponding acid in the form of a salt, such as an alkali metal salt, for example, the sodium salt with 1.5 to 2.5 equivalents of an appropriate alkanoylaminomethyl halide or alkoxycarbonylaminomethyl halide each of which may be represented by the structure:

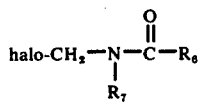

wherein halo is selected from a reactive halogen atom such as chlorine or bromine, $R_6$ is selected from a straight or branched lower alkyl group of from 1 to 4 carbon atoms or a straight or branched lower alkoxy group of from 1 to 4 carbon atoms, and $R_7$ is hydrogen or a lower alkyl group of from 1 to 4 carbon atoms. The reactants are stirred for about 1 to 5 hours in dimethylformamide, hexamethylformamide or a similar solvent at a temperature ranging from 10° to 45° C after which the reaction mixture is poured into ice water and decanted. The oily residue is taken up in an organic solvent such as ethylacetate, methylene chloride or benzene, washed with base then with water and dried over magnesium sulfate. The organic solution is evaporated to dryness in vacuo to give the desired ester.

Prior to the above esterification reaction, compounds wherein W represents amino are protected with blocking groups for example, tert-butoxycarbonyl or carbobenzyloxy, such groups being removed on completion of the esterification procedure by methods generally known in the art, for example, by the methods set forth in the aforementioned U.S. Pat. No. 3,657,232.

Compounds of this invention wherein M represents p-(alkanoyloxy)benzyl, and W is other than COOH may also be prepared by reacting molar equivalents of the corresponding acid and a p-(alkanoyloxy)benzyl alcohol wherein the alkanoyl moiety contains from 1 to 4 carbon atoms and may be straight or branched. The reactants are dissolved in an organic solvent such as dimethylformamide or hexamethylphosforamide and cooled to a temperature of from −15° to 25° C after which an equivalent quantity of dicyclohexylcarbodiimide in dimethylformamide or hexamethylphosphoramide is added dropwise to the reaction mixture with stirring. Stirring is continued for 1/2 to 2 hours at temperatures of from −15° to 25° C and then 4 to 6 hours at from 25° to 45° C. The formed dicyclohexylurea is removed by filtration, and the filtrate is diluted with chloroform, ethylacetate or methylene chloride and washed with water. The organic layer is dried and evaporated to give the product.

Compounds of this invention wherein M is alkanoyloxymethyl, and W is other than COOH may also be prepared by reacting the corresponding acid in the form of a salt, such as, an alkali metal salt or the triethylammonium salt with a compound of the formula:

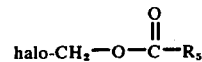

wherein halo is chlorine or bromine, and $R_5$ is a straight or branched lower alkyl group of from 1 to 4 carbon atoms by the general procedure described in U.S. Pat. No. 3,655,658.

Compounds of this invention wherein M is aminoalkanoyloxymethyl, and W is other than COOH may also be prepared by mixing a suspension of the sodium salt of the corresponding acid and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride, washed with water, aqueous base, then water. The organic phase is separated and the precipitate isolated by conventional means followed by deprotection of the amine group to give the product.

Compounds of this invention wherein $R_3$ is hydrogen may also be prepared by solvolysis of a compound of the formula

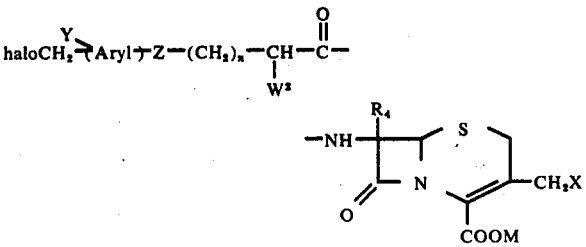

Formula XII wherein Aryl, Y, Z, $n$, $R_4$, M and X have the meanings defined in general Formula I; halo is chlorine or bromine; and $W^2$ is hydrogen, methyl, amino, hydroxy, $SO_3H$ or COOH; with a compound of general Formula VIII or a salt thereof in a solvent such as a lower alcohol, for example, methanol, ethanol, isopropyl alcohol, n-butanol or dimethylsulfoxide, dimethylformamide or aqueous mixtures of these solvents. The reaction is carried out for from 1/2 hour to 24 hours at a temperature of from 0° C to 125° C. The products are isolated by conventional means. This procedure is less preferred when the solution of the salt of the compound of Formula VIII is strongly basic.

Compounds of Formula XII are obtained by coupling a compound of Formula VII or a reactive derivative thereof with a compound of Formula V by conventional procedures.

EXAMPLE 1 p-Chloromethylphenylacetyl chloride

At a temperature of from −10° to 0° C hydrogen chloride gas is bubbled through a stirred mixture of 102 g of phenylacetic acid, 67.5 g of paraformaldehyde and 67.5 g of zinc chloride in 1000 ml of petroleum ether for one hour. Stirring is continued for about one hour at room temperature after which the mixture is refluxed for about 2 hours during which time hydrogen chloride gas is bubbled into the mixture. To the reaction mixture is added 1000 ml each of methylene chloride and water. The organic phase is separated and the aqueous phase is extracted twice with methylene chloride. The combined organic phases are extracted four times with a saturated sodium bicarbonate solution. The organic neutral phase is dried over anhydrous sodium sulfate, filtered and the solvent is removed under vacuum to give a neutral by-product which is further identified in Example 5 below. The basic aqueous phase is separated and acidified with cold concentrated hydrochloric acid to pH 2–3, then extracted three times with methylene chloride. The methylene chloride fraction is dried over anhydrous sodium sulfate, filtered and the solvent evaporated. The resulting oily acidic product is chromatographed on silica gel using benzene and benzene-acetone as the eluant to give p-chloromethylphenylacetic acid which is recrystallized from hot chloroform. M.P. 147°–149° C.

When in Example 1 an acid selected from Table I is substituted for phenylacetic acid in the respective chloromethyl derivative listed in Table I is obtained which can be converted to the acid chloride by the procedure of Example 1 (B).

TABLE I

| Acid | Chloromethyl derivative |
|---|---|
| hydrotropic acid | p-chloromethylhydrotropic acid |
| mandelic acid | p-chloromethylmandelic acid |
| dihydrocinnamic acid | p-chloromethyldihydrocinnamic acid |
| 2-methylhydrocinnamic acid | p-chloromethyl-2-methylhydrocinnamic acid |
| 3-phenyllactic acid | 3-(p-chloromethylphenyl)lactic acid |
| 4-phenylbutyric acid | 4-(p-chloromethylphenyl)butyric acid |
| 2-methyl-4-phenylbutyric acid | 2-methyl-4-(p-chloromethylphenyl)butyric acid |
| 2-hydroxy-4-phenylbutyric acid | 2-hydroxy-4-(p-chloromethylphenyl)butyric acid |
| phenoxyacetic acid | p-chloromethylphenoxyacetic acid |
| 2-phenoxypropionic acid | 2-(p-chloromethylphenoxy)propionic acid |
| 4-phenoxybutyric acid | 4-(p-chloromethylphenoxy)butyric acid |
| 2-methyl-4-phenoxybutyric acid | 2-methyl-4-(p-chloromethylphenoxy)butyric acid |
| 3-phenoxypropionic acid | 3-(p-chloromethylphenoxy)propionic acid |
| 3-phenoxylactic acid | 3-(p-chloromethylphenoxy)lactic acid |
| anilinoacetic acid | p-chloromethylanilinoacetic acid |
| 2-hydroxy-2-(2-thienyl)acetic acid | 2-hydroxy-2-[2-(5-chloromethyl)thienyl]acetic acid |
| 2-anilinopropionic | 2-(p-chloromethyl)anilinopropionic acid |
| 4-anilinobutyric acid | 4-(p-chloromethylanilino)butyric acid |
| 3-anilinobutyric acid | 3-(p-chloromethylanilino)butyric acid |
| phenylthioacetic acid | p-chloromethylphenylthioacetic acid |
| 2-phenylthiopropionic acid | 2-(p-chloromethylphenyl)thiopropionic acid |
| 4-phenylthiobutyric acid | 4-(p-chloromethylphenyl)thiobutyric acid |
| o-chlorophenylacetic acid | o-chloro-p-chloromethylphenylacetic acid |

EXAMPLE 2 p-Chloromethylphenylglycine

A mixture of 2.03 g of trifluoroacetylated phenylglycine, 0.8 g of zinc chloride in chloromethylether is heated at 65° C for 12 hours. The excess reagent is removed under vacuum, and the residue is dissolved in $CH_2Cl_2$, washed with saturated $NaHCO_3$ solution then saturated sodium chloride solution. The neutral organic phase is dried over $Na_2SO_4$ and concentrated to an oil which was purified by column chromatography, yielding the methyl ester of p-chloromethylphenylglycine which on hydrolysis with aqueous hydrochloric acid yields the acid hydrochloride. The acid hydrochloride can be converted to the free acid by adjusting the pH of the aqueous solution to about 5. Similarly, the chloromethyl derivatives listed in Table II may be prepared from the listed acid.

TABLE II

| Acid | Chloromethyl derivative |
|---|---|
| phenylalanine | p-(chloromethylphenyl)alanine |
| 2-amino-4-phenylbutyric acid | 2-amino-4-(p-chloromethylphenyl)butyric acid |
| 2-amino-4-phenoxybuytric acid | 2-amino-4-(p-chloromethylphenoxy)butyric acid |
| 3-phenoxyalanine | 3-(p-chloromethylphenoxy)alanine |
| 2-amino-4-anilinobutyric acid | 2-amino-4-(p-chloromethylanilino)butyric acid |
| 2-amino-4-phenylthiobutyric acid | 2-amino-4-(p-chloromethylphenyl)thiobutyric acid |
| 3-phenylthioalanine | 3-(p-chloromethylphenyl)thioalanine |
| 2-(2-thienyl)glycine | 2-[2-(5-chloromethyl)thienyl]glycine HCl |
| 2-amino-3-(2-thienyl)propionic acid | 2-amino-3-[2-(5-chloromethyl)thienyl]propionic acid |
| 2-amino-4-(2-thienyl)butyric acid | 2-amino-4-[2-(5-chloromethyl)thienyl]butyric acid |

EXAMPLE 3 p-Chloromethylphenylmalonic acid

When in the procedure of Example 1 (A) an equivalent amount of phenylmalonic acid diethyl ester is substituted for phenylacetic acid, p-chloromethylphenylmalonic acid diethyl ester is obtained which yields the corresponding acid upon acid hydrolysis. In a similar manner the chloromethyl derivatives listed in Table III may be prepared when the diethyl ester of the corresponding acid listed in Table III is substituted for phenylmalonic acid diethyl ester.

TABLE III

| Acid | Chloromethyl derivative |
|---|---|
| 2-sulfophenylacetic acid | 2-sulfo-p-chloromethylphenylacetic acid |
| 3-phenyl-2-sulfopropionic acid | 3-(p-chloromethylphenyl)-2-sulfopropionic acid |
| 4-phenyl-2-sulfobutyric acid | 4-(p-chloromethylphenyl)-2-sulfobutyric acid |
| benzylmalonic acid | p-chloromethylbenzylmalonic acid |
| phenethylmalonic acid | p-chloromethylphenethylmalonic acid |
| 2-phenoxyethylmalonic acid | 2-(p-chloromethylphenoxy)ethylmalonic acid |
| 2-phenylthioethyl- | 2-(p-chloromethyl- |

TABLE III-continued

| Acid | Chloromethyl derivative |
|---|---|
| malonic acid | phenyl)thioethyl-malonic acid |
| anilinomethyl-malonic acid | p-chloromethylanilinomethylmalonic acid |
| 2-thienylmalonic acid | 2-[2-(5-chloromethyl)-thienyl]malonic acid |
| 2-thenylmalonic acid | 2-[2-(5-chloromethyl)-thenyl]malonic acid |

EXAMPLE 4

5-(Chloromethyl-2-thienylacetic acid

2-Thiophenecarboxylic acid is treated in a solution of chloroform with chloromethyl ether in the presence of 0.9 to 2.2 equivalents of aluminum chloride to give 5-chloromethyl-2-thienylcarboxylic acid. Treatment of the obtained acid with excess thionyl chloride at room temperature for about 16 hours yields the acid chloride with is reacted with diazomethane to give the corresponding diazoketone. A methanol solution of the diazoketone is irradiated under nitrogen for about one hour with a high pressure mercury lamp using a Quarz filter. The methyl 5-chloromethyl-2-thienylacetate is obtained upon work up and column chromatography on silica gel. The acetate is hydrolyzed by treatment of a 1:1 mixture of acetic acid and concentrated hydrochloric acid at room temperature overnight to give 5-chloromethyl-2-thienylacetic acid.

EXAMPLE 5 o-Hydroxymethylphenylacetic acid lactone

The neutral by-product obtained in Example 1 is purified by sublimation under vacuum (0.05 mm Hg at 80° C) to give o-hydroxymethylphenylacetic acid lactone. M.P. 82° C.

EXAMPLE 6 o-Bromomethylphenylacetic acid

To a solution of 5 ml of glacial acetic acid saturated with hydrogen bromide gas is added at 0° C a solution of o-hydroxymethylphenylacetic acid lactone (0.55 g) in 2 ml of glacial acetic acid. The mixture is stirred at room temperature for two hours then refluxed for one hour during which time hydrogen bromide gas is bubbled into the mixture. The excess lactone and solvent are removed under high vacuum at room temperature. The resulting oily residue is triturated three times with hexane to give o-bromomethylphenylacetic acid. M.P. 110° C.

EXAMPLE 7 o-Chloromethyl-p-methoxymandelic acid chloride

The above-named acid is obtained by the procedure described by B. Reichert et al., Pharmazie 5, 10 (1950) and is converted to the acid chloride by treatment with thionyl chloride.

EXAMPLE 8

3-[(Acetyloxy)methyl]-7-amino-8-oxo-5-thia-1-azabicyclo-[4.2.0]oct-2-ene-2-carboxylic acid propionyloxymethyl ester To 35 ml of dimethyl formamide is added 7.5 g of the sodium salt of 3-[(acetyloxy)methyl]-7-amino-8-oxo-5-thia-1-azabicyclo[4.2.0]oct-2-ene-2-carboxylic acid, and the solution is stirred at room temperature for about 30 minutes after which 8 ml of chloromethylpropionate is added. Stirring is continued at room temperature for about 3 hours. The mixture is diluted with ethyl acetate and washed with water. The organic layer is separated and evaporated to dryness. The residue is recrystallized from ethyl acetate to give 3-[(acetyloxy)-methyl]-7-amino-8-oxo-5-thia-1-azabicyclo[4.2.0]oct-2-ene-2-carboxylic acid propionyloxymethyl ester In a similar manner when an appropriate amount of chloromethylpivalate, chloromethylacetate or chloromethylbutyrate is substituted for chloromethylpropionate, the following respective products are obtained:

3-[(acetyloxy)methyl]-7-amino-8-oxo-5-thia-1-azabicyclo[4.2.0]oct-2-ene-2-carboxylic acid pivalyloxymethyl ester, 3-[(acetyloxy)methyl]-7-amino-8-oxo-5-thia-1-azabicyclo[4.2.0]oct-2-ene-2-carboxylic acid acetyloxymethyl ester, 3-[(acetyloxy)methyl]-7-amino-8-oxo-5-thia-1-azabicyclo[4.2.0]oct-2-ene-2-carboxylic acid butyryloxymethyl ester.

EXAMPLE 9

3-[(Acetyloxy)methyl]-7-amino-8-oxo-5-thia-1-azabicyclo-[4.2.0]oct-2-ene-2-carboxylic acid 2-amino-3-methylbutyryloxymethyl ester A suspension of 5 grams of 3-[(acetyloxy)methyl]-7-amino-8-oxo-5-thia-1-azabicyclo[4.2.0]oct-2-ene-2-carboxylic acid sodium salt and 8.5 grams of N-tert-butoxycarbonyl-L-valine chloromethyl ester, which is prepared by the general procedure described in W. German Offen. 2,236,620, are mixed in 100 ml of dimethyl formamide and stirred for 72 hours. The mixture is diluted with ethyl acetate, washed with water with aqueous bicarbonate and again with water. The organic layer is dried over magnesium sulfate, filtered, and evaporated to dryness to give 3-[(acetyloxy)methyl]-7-amino-8-oxo-5-thia-1-azabicyclo[4.2.0]oct-2-ene-2-carboxylic acid N-tert-butoxycarbonyl-2-amino-3-methylbutyryloxymethyl ester from which the amine protecting group is removed by standard procedures to give the title product.

EXAMPLE 10

3-[(Acetyloxy)methyl]-7-amino-8-oxo-5-thia-1-azabicyclo-[4.2.0]oct-2-ene-2-carboxylic acid N-ethoxycarbonyl-N-methylaminomethyl ester 725 mg (2.5 mM) of the sodium salt of 3-[(acetyloxy)methyl]-7-amino-8-oxo-5-thia-1-azabicyclo[4.2.-0]oct-2-ene-2-carboxylic acid in 50 ml of dimethyl formamide is treated at room temperature with 375 mg (2.5 mM) of N-chloromethyl-N-methylurethane for one hour. The mixture is carefully poured into ice water and the precipitated solid is removed by filtration and washed with water. The solid is dissolved in ethylacetate and washed with aqueous sodium bicarbonate and then with water. The organic layer is dried over magnesium sulfate filtered and evaporated to dryness in vacuo to give 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester.

When in the above procedure an appropriate amount of N-methyl-N-propionylaminomethyl chloride, N-butyrylaminomethyl chloride, N-acetylaminomethyl chloride, or N-methyl-N-ethoxycarbonylaminomethyl chloride is substituted for N-chloromethyl-N-methylurethane the following respective compounds are obtained.

3-[(acetyloxy)methyl]-7-amino-8-oxo-5-thia-1-azabicyclo-[4.2.0]oct-2-ene-2-carboxylic acid N-methyl-N-propionylaminomethyl ester, 3-[(acetyloxy)methyl]-7-amino-8-oxo-5-thia-1-azabicyclo-[4.2.0]oct-2-ene-2-carboxylic acid N-butyrylaminomethyl ester, 3-[(acetyloxy)methyl]-7-amino-8-oxo-5-thia-1-azabicyclo-[4.2.0]oct-2-ene-2-carboxylic acid N-acetylaminomethyl ester and, 3-[(acetyloxy)methyl]-7-amino-8-oxo-5-thia-1-azabicyclo-[4.2.0]oct-2-ene-2-carboxylic acid N-methyl-N-ethoxycarbonylaminomethyl ester.

EXAMPLE 11

3-[(Acetyloxy)methyl]-7-amino-8-oxo-5-thia-1-azabicyclo[4.2.0]oct-2-ene-2-carboxylic acid p-pivalyloxybenzyl ester To a suspension of 6.6 mM of 3-[(acetyloxy)methyl]-7-amino-8-oxo-5-thia-1-azabicyclo[4.2.0]oct-2-ene-2-carboxylic acid sodium salt in 35 ml of dimethyl formamide (DMF) is added 2 equivalents of p-pivalyloxybenzyl alcohol followed by cooling to 0° C after which 7.2 mM of dicyclohexylcarbodiimide in 7.5 ml of DMF is added dropwise with stirring. The mixture is stirred at 0° C for one hour and an additional four hours at room temperature. The formed dicyclohexylurea is removed by filtration. The filtrate is diluted with chloroform, washed with water, dried over magnesium sulfate, filtered, and evaporated in vacuo to give 3-[(acetyloxy)-methyl]-7-amino-8-oxo-5-thia-1-azabicyclo[4.2.0]oct-2-ene-2-carboxylic acid p-pivalyloxybenzyl ester.

When in the above procedure an appropriate amount of p-(propionyloxy)benzyl alcohol, p-(acetyloxy)benzyl alcohol, or p-(valeryloxy)benzyl alcohol is substituted for p-pivalyloxybenzyl alcohol the following respective products are obtained:

3-[(acetyloxy)methyl]-7-amino-8-oxo-5-thia-1-azabicyclo-[4.2.0]oct-2-ene-2-carboxylic acid p-(propionyloxy)benzyl ester, 3-[(acetyloxy)methyl]-7-amino-8-oxo-5-thia-1-azabicyclo-[4.2.0]oct-2-ene-2-carboxylic acid p-(acetyloxy)benzyl ester, and 3-[(acetyloxy)methyl]-7-amino-8-oxo-5-thia-1-azabicyclo-[4.2.0]oct-2-ene-2-carboxylic acid p-(valeryloxy)benzyl ester.

EXAMPLE 12

3-[(2-Methyl-1,3,4-thiadiazol-5-ylthio)methyl]-7-amino-8-oxo-5-thia-1-azabicyclo[4,2,0]oct-2-ene-2-carboxylic acid In about 1 liter of water is dissolved 0.1 mole of the sodium salt of 3-[(acetyloxy)methyl]-7-amino-8-oxo-5-thia-1-azabicyclo[4.2.0]oct-2-ene-2-carboxylic acid at 70° C under nitrogen atmosphere. To the solution is added 1 equivalent of sodium bicarbonate and 2 equivalents of 2-methyl-1,3,4-thiadiazol-5-ylthiol. The mixture is stirred at 70° C for 3 hours after which the pH is adjusted to 3.5, and the resulting precipitate collected giving 3-[(2-methyl-1,3,4-thiadiazol-5-ylthio)methyl]-7-amino-8-oxo-5-thia-1-azabicyclo[4.2.0]oct-2-ene-2-carboxylic acid.

When in the above procedure an equivalent amount of 1,3,4-thiadiazol-5-ylthiol, 3-methyl-1,2,4-thiadiazol-5-ylthiol, tetrazol-5-ylthiol, 1-methyltetrazol-5-ylthiol, 2-methyl-1,3,4-oxadiazol-5-ylthio, or 1,2,3-triazol-5-ylthiol is substituted for 2-methyl-1,3,4-thiadiazol-5-ylthiol the following respective products are obtained:

3-[(1,3,4-thiadiazol-5-ylthio)methyl]-7-amino-8-oxo-5-thia-1-azabicyclo[4.2.0]oct-2-ene-2-carboxylic acid, 3-[(3-methyl-1,2,4-thiadiazol-5-ylthio)methyl]-7-amino-8-oxo-5-thia-1-azabicyclo[4,2.0]oct-2-ene-2-carboxylic acid, 3-[(tetrazol-5-ylthio)methyl]-7-amino-8-oxo-5-thia-1-azabicyclo-[4.2.0]oct-2-ene-2-carboxylic acid, 3-[(1-methyltetrazol-5-ylthio)methyl]-7-amino-8-oxo-5-thia-1-azabicyclo[4.2.0]oct-2-ene-2-carboxylic acid, 3-[(2-methyl-1,3,4-oxadiazol-5-ylthio)methyl]-7-amino-8-oxo-5-thia-1-azabicyclo[4.2.0]oct-2-ene-2-carboxylic acid, and 3-[(1,2,3-triazol-5-ylthio)methyl]-7-amino-8-oxo-5-thia-1-azabicyclo[4.2.0]oct-2-ene-2-carboxylic acid.

When the procedure of Example 8 appropriate amounts of 3-methyl-7-amino-8-oxo-5-thia-1-azabicyclo[4.2.0]oct-2-ene-2-carboxylic acid and chloromethylpivalate are substituted respectively for 3-[(acetyloxy)methyl]-7-amino-8-oxo-5-thia-1-azabicyclo[4.2.0]oct-2-ene-2-carboxylic acid and chloromethylpropionate, 3-methyl-7-amino-8-oxo-5-thia-1-azabicyclo[4.2.0]oct-2-ene-2-carboxylic acid pivalyloxymethyl ester is obtained.

EXAMPLE 13

When in the procedure of Example 12 appropriate amounts of the sodium salt of the cephalosporin derivative and the heterocyclicthiol derivative listed below in Table IV are substituted respectively for the sodium salt of 3-[(acetyloxy)methyl]-7-amino-8-oxo-5-thia-1-azabicyclo[4.2.0]oct-2-ene-2-carboxylic acid and 2-methyl-1,3,4-thiadiazol-5-ylthiol the respective products listed in Table IV are obtained.

TABLE IV

| Cephalosporin Derivative | Heterocyclicthiol | Product |
| --- | --- | --- |
| 3-[acetyloxy)methyl]-7-amino-8-oxo-5-thia-1-azabicyclo[4.2.0]oct-2-ene-2-carboxylic acid propionyloxymethyl ester | 3-methyl-1,2,4-thiadiazol-5-ylthio | 3-[(3-methyl-1,2,4-thiadiazol-5-ylthio)methyl]-7-amino-8-oxo-5-thia-1-azabicyclo[4.2.0]oct-2-ene-2-carboxylic acid propionyloxymethyl ester |
| 3-[(acetyloxy)methyl]-7-amino-8-oxo-5-thia-1-azabicyclo[4.2.0]oct-2-ene-2-carboxylic acid p-pivalyloxymethyl ester | 1-methyltetrazol-5-ylthiol | 3-[(1-methyltetrazol-5-ylthio)methyl]-7-amino-8-oxo-5-thia-1-azabicyclo-[4.2.0]oct-2-ene-2-carboxylic acid pivalyloxymethyl ester |
| 3-[(acetyloxy)methyl]-7-amino-8-oxo-5-thia-1-azabicyclo[4.2.0]oct-2-ene-2-carboxylic acid acetyloxymethyl | 1,3,4-thiadiazol-5-ylthiol | 3-[(1,3,4-thiadiazol-5-ylthio)methyl]-7-amino-8-oxo-5-thia-1-azabicyclo-[4.2.0]oct-2-ene-2-carboxylic acid |

TABLE IV-continued

| Cephalosporin Derivative | Heterocyclicthiol | Product |
|---|---|---|
| ester | | acetyloxymethyl ester |
| 3-[(acetyloxy)methyl]-7-amino-8-oxo-5-thia-1-azabicyclo[4.2.0]oct-2-ene-2-carboxylic acid butyryloxymethyl ester | tetrazol-5-ylthiol | 3-[(tetrazol-5-ylthio)methyl]-7-amino-8-oxo-5-thia-1-azabicyclo[4.2.0]oct-2-ene-2-carboxylic acid butyryloxymethyl ester |
| 3-[(acetyloxy)methyl]-7-amino-8-oxo-5-thia-1-azabicyclo[4.2.0]oct-2-ene-2-carboxylic acid 2-amino-3-methylbutyryloxymethyl ester | 2-methyl-1,3,4-oxadiazol-5-ylthiol | 3-[(2-methyl-1,3,4-oxadiazol-5-ylthio)methyl]-7-amino-8-oxo-5-thia-1-azabicyclo[4.2.0]oct-2-ene-2-carboxylic acid 2-amino-3-methylbutyryloxymethyl ester |
| 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 2-methyl-1,3,4-thiadiazol-5-ylthio | 3-[(2-methyl-1,3,4-thiadiazol-5-ylthio)methyl]-7-amino-8-oxo-5-thia-1-azabicyclo[4.2.0] oct-2-ene-2-carboxylic acid N-ethoxycarbonyl-N-methylaminomethyl ester |
| 3-[(acetyloxy)methyl]-7-amino-8-oxo-5-thia-1-azabicyclo[4.2.0]oct-2-ene-2-carboxylic acid p-pivalyloxybenzyl ester | 1-methyltetrazol-5-ylthiol | 3-[(1-methyltetrazol-5-ylthio)methyl]-7-amino-8-oxo-5-thia-1-azabicyclo[4.2.0]oct-2-ene-2-carboxylic acid p-pivalyloxybenzyl ester |
| 3-[(acetyloxy)methyl]-7-amino-7-methoxy-8-oxo-5-thia-1-azabicyclo[4.2.0]oct-2-ene-2-carboxylic acid (prepared by acid hydrolysis of the corresponding benzhydryl ester described in U.S. Pat. No. 3,778,432) | 2-methyl-1,3,4-thiadiazol-5-ylthiol | 3-[(2-methyl-1,3,4-thiadiazol-5-ylthio)methyl]-7-amino-7-methoxy-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]oct-2-ene-2-carboxylic acid p-(propionyloxy)benzyl ester | 1-methyltetrazol-5-ylthiol | 3-[(1-methyltetrazol-5-ylthio)methyl]-7-amino-8-oxo-5-thia-1-azabicyclo[4.2.0]oct-2-ene-2-carboxylic acid p-(propionyloxy)benzyl ester |
| 3-[(acetyloxy)methyl]-7-amino-8-oxo-5-thia-1-azabicyclo[4.2.0]oct-2-ene-2-carboxylic acid p-(acetyloxy)benzyl ester | tetrazol-5-ylthiol | 3-[(tetrazol-5-ylthio)methyl]-7-amino-8-oxo-5-thia-1-azabicyclo[4.2.0]oct-2-ene-2-carboxylic acid p-(acetyloxy)benzyl ester |
| 3-[(acetyloxy)methyl]-7-amino-8-oxo-5-thia-1-azabicyclo[4.2.0]oct-2-ene-2-carboxylic acid p-(valeryloxy)benzyl ester | 3-methyl-1,2,4-thiadiazol-5-ylthiol | 3-[(3-methyl-1,2,4-thiadiazol-5-ylthio)methyl]-7-amino-8-oxo-5-thia-1-azabicyclo[4.2.0]oct-2-ene-2-carboxylic acid p-(valeryoxy)benzyl ester |

EXAMPLE 14 p-(N,N-diethyldithiocarbamatemethyl)phenylacetic acid

A solution of 1.22 g (5.5 m mole) of sodium diethyldithiocarbamatetrihydrate and 463 mg (2.5 m mole) of 4-chloromethylphenylacetic acid in 10 ml of methanol was stirred overnight at room temperature. The residue was dissolved in 15 ml of water, acidified with 10% aqueous hydrochloric acid to pH 1, extracted with 50 ml of ether, washed three times with water and dried over anhydrous magnesium sulfate. The ether was evaporated, and the residue recrystallized from ether-hexane to give P-(N,N-diethyldithiocarbamatemethyl)-phenylacetic acid. M.P. 96° C.

EXAMPLE 15 p-(Dithiocarbamatemethyl)phenylacetic acid

A solution of 75 mg (2.5 m mole) of freshly prepared ammonium dithiocarbamate and 184.5 mg (1 m mole) of 4-chloromethylphenylacetic acid in 10 ml of methanol was stirred at room temperature under nitrogen atmosphere. The solvent was evaporated and the residue was dissolved in water. The aqueous solution was acidified to pH 1 with aqueous hydrochloric acid, extracted with ethylacetate, dried over anhydrous magnesium sulfate and evaporated. The residue was recrystallized from ethylacetate-hexane to give p-(dithiocarbamatemethyl)phenylacetic acid. M.P. 168° C.

EXAMPLE 16 p-(Morpholinodithiocarbamatemethyl)phenylacetic acid

A solution of 1.85 g (0.01 mole) of 4-chloromethylphenyl acetic acid and 6.25 g (0.025 mole) of freshly prepared morpholinodithiocarbamate salt in 250 ml of methanol was stirred under nitrogen for 20 hours at room temperature. The solvent was evaporated, water was added and the solution was acidified to pH 1 using aqueous 10% hydrochloric acid then extracted with ethylacetate, dried over anhydrous magnesium sulfate and evaporated. The residue was recrystallized from ethylacetate to give p-morpholinodithiocarbamatemethyl)phenylacetic acid. M.P. 163° C.

EXAMPLE 17 p-(Morpholinomonothiocarbamatemethyl)phenylacetic acid

Morpholinomonothiocarbamate morpholine salt was prepared by modification of the synthesis described by J. Parrod, Compt. rend. 234, 1062 (1952). Carbonylsulfide was passed through a trap cooled to −78° C to assure the condensation of carbondisulfide and bubbled into a solution of morpholine (8.7 g) in 150 ml of ethanol at 0° C. The precipitate was filtered, washed with cold ethanol and 7.5 g (0.032 mole) of the thus obtained morpholinomonothiocarbamate morpholine salt was immediately combined with 1.85 g (0.01 mole)

of chloromethylphenylacetic acid in 100 ml of dry methanol and stirred under nitrogen for 20 hours. The methanol was evaporated, the residue dissolved in water and acidified to pH 1 using aqueous 10% hydrochloric acid then extracted with ethylacetate (400 ml) and dried over anhydrous magnesium sulfate. The solvent was removed and the residue was recrystallized from ethylacetate to give p-morpholinomonothiocarbamatemethyl)phenylacetic acid. M.P. 181°–182° C.

Following the procedure of Example 14 only substituting for sodium diethyldithiocarbamatetrihydrate an appropriate amount of sodium salt of di-n-propyldithiocarbamate, di-ni-butyldithiocarbamate, pyrrolidinodithiocarbamate or piperidinodithiocarbamate the following respective acids are obtained:
p-(N,N-di-n-propyldithiocarbamatemethyl)phenylacetic acid,
p-(N,N-di-n-butyldithiocarbamatemethyl)phenylacetic acid,
p-(pyrrolidinodithiocarbamatemethyl)phenylacetic acid, and
p-(piperidinodithiocarbamatemethyl)phenylacetic acid.

Following the procedure of Example 17 only substituting an appropriate amount of monothiocarbamateamine salt, dimethylmonothiocarbamate dimethylamine salt, diethylmonothiocarbamate diethylamine salt, di-n-propylmonothiocarbamate di-n-propylamine salt, di-n-butylmonothiocarbamate di-n-butylamine salt, pyrrolidinomonothiocarbamate pyrrolidine salt or piperidinomonothiocarbamate piperidine salt for morpholinomonothiocarbamate morpholine salt the following respective products are obtained:
p-(monothiocarbamatemethyl)phenylacetic acid,
p-(N,N-dimethylmonothiocarbamatemethyl)phenylacetic acid,
p-(N,N-diethylmonothiocarbamatemethyl)phenylacetic acid,
p-(N,N-di-n-propylmonothiocarbamatemethyl)phenylacetic acid,
p-(N,N-di-n-butylmonothiocarbamatemethyl)phenylacetic acid,
p-(pyrrolidinomonothiocarbamatemethyl)phenylacetic acid, and
p-(piperidinomonothiocarbamatemethyl)phenylacetic acid.

Following the general procedure of Example 15, by reaction of appropriate amount of the chloromethyl acid derivatives and carbamate listed in the following Table V the respective carbamatemethyl substituted acids listed in Table V are obtained. Although other salts may be used, the sodium salt of the carbamate reactant is employed except that in the case of the morpholinodi- and mono-thiocarbamate and the piperidino di- and mono-thiocarbamate the respective morpholine and piperidine salts are used.

TABLE V

| CHLOROMETHYL SUBSTITUTED ACIDS | CARBAMATE | CARBAMATE METHYL SUBSTITUTED ACIDS |
| --- | --- | --- |
| p-chloromethylhydrotropic acid | dithiocarbamate | p-(dithiocarbamatemethyl)hydrotropic acid |
| p-chloromethylmandelic acid | dimethyldithiocarbamate | p-(N,N-dimethyldithiocarbamatemethyl)mandelic acid |
| p-chloromethyldihydrocynnamic acid | diethyldithiocarbamate | p-(N,N-diethyldithiocarbamatemethyl)dihydrocynnamic acid |
| p-chloromethyl-2-methylhydrocynnamic acid | di-n-propyldithiocarbamate | p-(N,N-di-n-propyldithiocarbamatemethyl)2-methylhydrocynnamic acid |
| 3-(p-chloromethylphenyl)lactic acid | di-n-butyldithiocarbamate | 3-[p-(N,N-di-n-butyldithiocarbamatemethyl)phenyl]lactic |
| 4-(p-chloromethylphenyl)butyric acid | pyrrolidinodithiocarbamate | 4-[p-(pyrrolidinodithiocarbamatemethyl)phenyl]butyric acid |
| 2-methyl-4-(p-chloromethylphenyl)-butyric acid | piperidinodithiocarbamate | 2-methyl-4-[p-(piperidinodithiocarbamatemethyl)phenyl]butyric acid |
| 2-hydroxy-4-(p-chloromethylphenyl)-butyric acid | morpholinodithiocarbamate | 2-hydroxy-4-[p-(morpholinodithiocarbamatemethyl)phenyl]butyric aci |
| p-chloromethylphenoxyacetic acid | monothiocarbamate acid | p-(monothiocarbamatemethyl)phenoxyacetic acid |
| 2-(p-chloromethylphenoxy)propionic acid | dimethylmonothiocarbamate | 2-[p-(N,N-dimethylmonothiocarbamatemethyl)phenoxy]propionic acid |
| 4-(p-chloromethylphenoxy)butyric acid | diethylmonothiocarbamate | 4-[p-(N,N-diethylmonothiocarbamatemethyl)phenoxy]butyric acid |
| 2-methyl-4-(p-chloromethylphenoxy)-butyric acid | di-n-propylmonothiocarbamate | 2-methyl-4-[p-(N,N-di-n-propylmonothiocarbamatemethyl)phenoxy]butyric aci |
| 3-(p-chloromethylphenoxy)propionic acid | di-n-butylmonothiocarbamate | 3-[p-(N,N-di-n-butylmonothiocarbamatemethyl)phenoxy]propionic acid |
| 3-(p-chloromethylphenoxy)lactic acid | pyrrolidinomonothiocarbamate | 3-[p-(pyrrolidinomonothiocarbamatemethyl)phenoxy]lactic acid |
| p-chloromethylanilinoacetic acid | piperidinomonothiocarbamate | p-(piperidinomonothiocarbamatemethyl)-anilinoacetic acid |
| 2-hydroxy-2-[5-(chloromethyl)-2-thienyl]acetic acid | morpholinomonothiocarbamate | 2-hydroxy-2-[5-(morpholinomonothiocarbamatemethyl)-2-thienyl]acetic acid |
| 2-(p-chloromethyl)anilinopropionic acid | morpholinomonothiocarbamate | 2-[p-(monothiocarbamatemethyl)anilino]propionic acid |

TABLE V-continued

| CHLOROMETHYL SUBSTITUTED ACIDS | CARBAMATE | CARBAMATE METHYL SUBSTITUTED ACIDS |
|---|---|---|
| 4-(p-chloromethylanilino)butyric acid | piperidinomonothiocarbamate | 4-[p-(piperidinomonothiocarbamate)-anilino]butyric acid |
| 3-(p-chloromethylanilino)butyric acid | pyrrolidinomonothiocarbamate | 3-[p-(pyrrolidinomonothiocarbamatemethyl)anilino]butyric acid |
| p-chloromethylphenylthioacetic acid | di-n-butylmonothiocarbamate | p-(N,N-di-n-butylmonothiocarbamatemethyl)phenylthioacetic acid |
| 2-(p-chloromethylphenyl)thiopropionic acid | di-n-propylmonothiocarbamate | 2-[p-(N,N-di-n-propylmonothiocarbamatemethyl)phenyl]thiopropionic acid |
| 4-(p-chloromethylphenyl)thiobutyric acid | diethylmonothiocarbamate | 4-[p-(N,N-diethylmonothiocarbamatemethyl)phenyl]thiobutyric acid |
| o-chloro-p-chloromethylphenylacetic acid | dimethylmonothiocarbamate | o-chloro-p-(N,N-dimethylmonothiocarbamatemethyl)phenylacetic acid |
| p-chloromethylphenylglycine | monothiocarbamate | p-(monothiocarbamatemethyl)phenylglycne |
| p-(chloromethylphenyl)alanine | morpholinodithiocarbamate | p-(morpholinodithiocarbamatemethyl)-phenylalanine |
| 2-amino-4-(p-chloromethylphenyl)butyric acid | piperidinodithiocarbamate | 2-amino-4-[p-(piperidinodithiocarbamatemethyl)phenyl]butyric acid |
| 2-amino-4-(p-chloromethylphenoxy)butyric acid | pyrroldinodithiocarbamate | 2-amino-4-[p-(pyrrolidinodithiocarbamatemethyl)phenoxy]butyric acid |
| 3-(p-chloromethylphenoxy)-alanine | di-n-butyldithiocarbamate | 3-[p-(N,N-di-n-butyldithiocarbamatemethyl)phenoxy]alanine |
| 2-amino-4-(p-chloromethylanilino)butyric acid carbamate | di-n-propyldithiocarbamatemethyl)anilino]-butyric acid | 2-amino-4-[p-N,N-di-n-propyldithio- |
| 2-amino-4-(p-chloromethylphenyl)thiobutyric acid | diethyldithiocarbamate | 2-amino-4-[p-(N,N-diethyldithiocarbamatemethyl)phenyl]thiobutyric acid |
| 3-(p-chloromethylphenyl)-thioalanine | dimethyldithiocarbamate | 3-[p-(N,N-dimethyldithiocarbamatemethyl)phenyl]thioalanine |
| 2-[2-(5-chloromethyl)thienyl]-glycine | dithiocarbamate | 2-[2-(5-dithiocarbamatemethyl)thienyl]-glycne |
| 2-amino-3-[2-(5-chloromethyl)-thienyl]propionic acid | dithiocarbamate | 2-amino-3-[2-(5-dithiocarbamatemethyl)-thienyl]propionic acid |
| 2-amino-4-[2-(5-chloromethyl)-thienyl]butyric acid | dimethyldithiocarbamate | 2-amino-4-[2-(5-N,N-dimethyldithiocarbamate)thienyl]butyric acid |
| p-chloromethylphenylmalonic acid | diethyldithiocarbamate | p-(N,N-diethyldithiocarbamatemethyl)phenylmalonic acid |
| 2-sulfo-p-chloromethylphenylacetic acid | di-n-propyldithiocarbamate | 2-sulfo-p-(N,N-di-n-propyldithiocarbamatemethyl)phenylacetic acid |
| 3-(p-chloromethylphenyl)-2-sulfopropionic acid | di-n-butyldithiocarbamate | 3-[p-(N,N-di-n-butyldithiocarbamatemethyl)phenyl]-2-sulfopropionic acid |
| 4-(p-chloromethylphenyl)-2-sulfobutyric acid | pyrrolidinodithiocarbamate | 4-[p-(pyrrolidinodithiocarbamatemethyl)phenyl]-2-sulfobutyric acid |
| p-chloromethylbenzylmalonic acid | piperidinodithiocarbamate | p-(piperidinodithiocarbamatemethyl)-benzylmalonic acid |
| p-chloromethylphenethylmalonic acid | morpholinodithiocarbamate | p-(morpholinodithiocarbamatemethyl)-phenethylmalonic acid |
| 2-(p-chloromethylphenoxy)ethylmalonic acid | monothiocarbamate | 2-[p-(monothiocarbamatemethyl)phenoxy]ethylmalonic acid |
| 2-(p-chloromethylphenyl)thioethylmalonic acid | dimethylmonothiocarbamate | 2-[p-(N,N-dimethylmonothiocarbamatemethyl)phenyl]thioethylmalonic acid |
| p-chloromethylanilinomethylmalonic acid | diethylmonothiocarbamate | p-(N,N-diethylmonothiocarbamatemethyl)-anilinomethylmalonic acid |
| 2-[2-(5-chloromethyl)thienyl]malonic acid | di-n-propylmonothiocarbamate | 2-[2-(5-N,N-di-n-propylmonothiocarbamatemethyl)thienyl]malonic acid |
| 2-[5-(chloromethyl)-2-thenyl]-malonic acid | di-n-butylmonothiocarbamate | 2-[5-(N,N-di-n-butylmonothiocarbamatemethyl)-2-thenyl]malonic acid |

EXAMPLE 18

3-[(Acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid A solution of 289 mg (1 m mole) of p-(N,N-diethyldithiocarbamatemethyl)phenylacetic acid and 120 mg (1 m mole) of pivalyl chloride in absolute tetrahydrofuran was cooled to 0° C after which 101 mg (1 m mole) of triethylamine was added and the mixture was stirred for 30 minutes. To the mixture was added a cold solution of 272 mg (1 m mole) of 3-[(acetyloxy)methyl]-7-amino-8-oxo-5-thia-1-azabicyclo[4.2.0]oct-2-ene-2-carboxylic acid and 101 mg (1 m mole) of triethylamine in 7 ml of dry methylene chloride was added. The resulting mixture was stirred for 30 minutes at 0° C and for 1 hour at room temperature after which the solvent was removed under vacuum. The residue was dissolved in ice water, acidified to pH 2 using aqueous 10% hydrochloric acid and extracted with 30 ml of ethylacetate. The organic layer was washed three times with water, dried over magnesium sulfate and evaporated leaving a residue that was triturated with dry ether, recrystallized from ethylacetate and precipitated with a mixture of ether and hexane to give 3-[(acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid. M.P. 138°–140° C (dec.).

EXAMPLE 19

3-[(Acetyloxy)methyl]-7-[[2-[4-(dithiocarbamatemethyl)phenyl]acetyl]amino]-8-oxo-5-thia-1-azabicyclo[4.2.0]oct-2-ene-2-carboxylic acid To a mixture of 60 mg (0.5 m mole) of pivalyl chloride and 50.5 mg (0.5 m mole) of triethylamine in 10 ml of dry tetrahydrofuran was added 120 mg (0.5 m mole) of p-(dithiocarbamatemethyl)phenylacetic acid. The mixture was stirred 30 minutes at 0° C after which a cold mixture of 136 mg (0.5m mole) of 3-[(acetyloxy)methyl]-7-amino-8-oxo-5-thia-1-azabicyclo[4.2.0]oct-2-ene-2-carboxylic acid and 75 mg (0.75 m mole) of triethylamine in 7 ml of dry methylene chloride was added. Stirring was continued for 30 minutes at 0° C and for 1 hour at room temperature. The solvent was evaporated, and 10 ml of cold water and 20 ml of ethylacetate were added. The mixture was acidified with cold aqueous 10% hydrochloric acid to pH 2 and extracted with ethylacetate. The organic layer was washed with water until the aqueous phase became neutral, dried over magnesium sulfate and evaporated. The residue was washed with ether and recrystallized from ethylacetate: ether-hexane to give 3-[(acetyloxy)methyl]-7-[[2-[4-(dithiocarbamatemethyl)phenyl]acetyl]-8-oxo-5-thia-1-azabicyclo[4.2.0]oct-2-ene-2-carboxylic acid.

EXAMPLE 20

3-[(Acetyloxy)methyl]-7-[[2-[4-(morpholinodithiocarbamatemethyl)phenyl]acetyl]amino]-8-oxo-5-thia-1-azabicyclo[4.2.0]oct-2-ene-2-carboxylic acid A cold solution of 544 mg (2 m mole) of 3-[(acetyloxy)methyl]-7-amino-8-oxo-5-thia-1-azabicyclo[4.2.0]oct-2-ene-2-carboxylic acid and 404 mg (4 m mole) of triethylamine in 20 ml of methylene chloride was slowly added with stirring to a solution of a mixed anhydride prepared from 622 mg (2 m mole) of p-(morpholinodithiocarbamatemethyl)phenylacetic acid, 241 mg (2 m mole) of pivalyl chloride and 202 mg (2 m mole) of triethylamine in 20 ml of tetrahydrofuran at 0° C. The stirring was continued for 30 minutes at 0° C and for 1 hour at room temperature. After which the solvent was evaporated and cold water added. The solution was acidifed to pH 2 using 10% aqueous hydrochloric acid and extracted with ethylacetate. The organic layer was washed with water, dried over magnesium sulfate and evaporated leaving a residue that was recrystallized from a hot mixture of 9 ml of chloroform, 9 ml of benzene and 2 ml of methanol yielding 3-[(acetyloxy)methyl]-7-[[2-[4-(morpholinodithiocarbamatemethyl)phenyl]acetyl]amino]-8-oxo-5-thia-1-azabicyclo[4.2.0]oct-2-ene-2-carboxylic acid. M.P. 164° C (dec.).

EXAMPLE 21

3-[(Acetyloxy)methyl]-7-[[2-[4-(morpholinomonothiocarbamatemethyl)phenyl]acetyl]amino]-8-oxo-5-thia-1-azabicyclo[4.2.0]oct-2-ene-2-carboxylic acid A cold solution of 544 mg (2 m mole) of 3-[(acetyloxy)methyl]-7-amino-8-oxo-5-thia-1-azabicyclo[4.2.0]oct-2-ene-2-carboxylic acid and 404 mg (4 m mole) of triethylamine in 20 ml of methylene chloride was slowly added with stirring to a solution of a mixed anhydride prepared from 590 mg (2 m mole) of p-(morpholinomonothiocarbamatemethyl)phenylacetic acid, 241 mg (2 m mole) of pivalyl chloride and 202 mg (2 m mole) of triethylamine in 20 ml of tetrahydrofuran at 0° C. Stirring was continued for 30 minutes at 0° C and for 1 hour at room temperature. The product was isolated by the general procedure described in Example 20 to give 3-[(acetyloxy)methyl]-7-[[2-[4-(morpholinomonothiocarbamatemethyl)phenyl]acetyl]amino]-8-oxo-5-thia-1-azabicyclo[4.2.0]oct-2-ene-2-carboxylic acid. M.P. 168° C.

When in the procedure of Example 18 an appropriate amount of an acid listed in the following Table VI is substituted for p-(N,N-diethyldithiocarbamatemethyl)phenylacetic acid the corresponding cephalosporin derivatives listed in Table VI is obtained.

Table VI

| ACID | CEPHALOSPORIN DERIVATIVE |
|---|---|
| p-(N,N-di-n-propyldithiocarbamatemethyl)phenylacetic acid | 3-[(acetyloxy)methyl]-7-[[2-[4-(N,N-di-n-propyldithiocarbamatemethyl)phenyl]acetyl]amino]-8-oxo-5-thia-1-azabicyclo[4.2.0]oct-2-ene-2-carboxylic acid |
| p-(N,N-di-n-butyldithiocarbamatemethyl)phenylacetic acid | 3-[(acetyloxy)methyl]-7-[[2-[4-(N,N-di-n-butyldithiocarbamatemethyl)phenyl]acetyl]amino]-8-oxo-5-thia-1-azabicyclo[4.2.0.]oct-2-ene- |

Table VI-continued

| ACID | CEPHALOSPORIN DERIVATIVE |
|---|---|
| | 2-carboxylic acid |
| p-(pyrrolidinothiocarbamate-methyl)phenylacetic acid | 3-[(acetyloxy)methyl]-7-[[2-[4-(pyrrolidinodithiocarbamatemethyl)phenyl]acetyl]amino]-8-oxo-5-thia-1-azabicyclo[4.2.0]oct-2-ene-2-carboxylic acid |
| p-(piperidinodithiocarbamate-methyl)phenylacetic acid | 3-[(acetyloxy)methyl]-7-[[2-[4-(piperidinodithiocarbamatemethyl)phenyl]acetyl]amino]-8-oxo-5-thia-1-azabicyclo[4.2.0.]oct-2-ene-2-carboxylic acid |
| p-(monothiocarbamatemethyl)-phenylacetic acid | 3-[(acetyloxy)methyl]-7-[[2-[4-(monothiocarbamatemethyl)-phenyl]acetyl]amino]-8-oxo-5-thia-1-azabicyclo[4.2.0]-oct-2-ene-2-carboxylic acid |
| p-(N,N-dimethylmonothiocarbamatemethyl)phenylacetic acid | 3-[(acetyloxy)methyl]-7-[[2-[4-(N,N-dimethylmonothiocarbamatemethyl)phenyl]acetyl]amino]-8-oxo-5-thia-1-azabicyclo[4.2.0]oct-2-ene-2-carboxylic acid |
| p-(N,N-diethylmonothio-carbamatemethyl)phenyl-acetic acid | 3-[(acetyloxy)methyl]-7-[[2-[4-(N,N-diethylmonothiocarbamatemethyl)phenyl]acetyl]amino]-8-oxo-5-thia-1-azabicyclo[4.2.0]oct-2-ene-2-carboxylic acid |
| p-(N,N-di-n-propylmono-thiocarbamatemethyl)-phenylacetic acid | 3-[(acetyloxy)methyl]-7-[[2-[4-(N,N-di-n-proplymonothio-carbamatemethyl)phenyl] acetyl]amino]-8-oxo-5-thia-1-azabicyclo[4.2.0]oct-2-ene-2-carboxylic acid |
| p-(N,N-di-n-butylmono-thiocarbamatemethyl)-phenylacetic acid tyl]amino]-8-oxo-5-thia-1- | 3-[(acetyloxy)methyl]-7-[[2-[4-(N,N-di-n-butylmonothio-carbamatemethyl)phenyl]ace-<br><br>azabicyclo[4.2.0]oct-2-ene-2-carboxylic acid |
| p-(pyrrolidinomonothio-carbamatemethyl)phenyl-acetic acid | 3-[(acetyloxy)methyl]-7-[[2-[4-(pyrrolidinomonothiocar-bamatemethyl)phenyl]acetyl]-amino]-8-oxo-5-thia-1-azabi-cyclo[4.2.0]oct-2-ene-2-car-boxylic acid |
| p-(piperidinomonothio-carbamatemethyl)phenyl-acetic acid | 3-[(acetyloxy)methyl]-7-[[2-[4-(piperidinomonothiocar-bamatemethyl)phenyl]acetyl]-amino]-8-oxo-5-thia-1-azabi-cyclo[4.2.0]oct-2-ene-2-car-boxylic acid |
| p-(dithiocarbamatemethyl)-hydrotropic acid | 3[(acetyloxy)methyl]-7-[[2-[4-(dithiocarbamatemethyl)-phenyl]-2-methylacetyl]amino]--8-oxo-5-thia-1-azabicyclo-[4.2.0]oct-2-ene-2-carbox-ylic acid |
| p-(N,N-dimethyldithiocar-bamatemethyl)mandelic acid | 3-[(acetyloxy)methyl]-7-[[2-[4-(N,N-dimethyldithiocar-bamatemethyl)thenyl]-2-hy-droxyacetyl]amino]-8-oxo-5-thia-1-azabicyclo[4.2.0.]-oct-2-ene-2-carboxylic acid |
| p-(N,N-diethyldithiocar-bamatemethyl)dihydro-cynnamic acid | 3-[(acetyloxy)methyl]-7-[[3-[4-(N,N-diethyldithiocarbam-atemethyl)thenyl]propionyl]-amino]-8-oxo-5-thia-1-azabi-cyclo[4.2.0]oct-2-ene-2-car-boxylic acid |
| p-(N,N-di-n-propyldithio-carbamatemethyl)2-methyl-hydrocynnamic acid | 3-[(acetyloxy)methyl]-7-[[3-[4-(N,N-di-n-propyldithio-carbamatemethyl)phenyl]-2-methylpropionyl]amino]-8-oxo-5-thia-1-azabicyclo-[4.2.0]oct-2-ene-2-carbox- |

Table VI-continued

| ACID | CEPHALOSPORIN DERIVATIVE |
|---|---|
| | ylic acid |
| 3-[p-(N,N-di-n-butyldi-thiocarbamatemethyl)-phenyl]lactic acid | 3-[(acetyloxy)methyl]-7-[[3-[4-(N,N-di-n-butyldithiocar-bamatemethyl)phenyl]-2-hydroxypropionyl]amino]-8-oxo-5-thia-1-azabicyclo-[4.2.0]oct-2-ene-2-carboxylic acid |
| 4-[p-(pyrrolidinodithio-carbamatemethyl)phenyl]-butyric acid | 3-[(acetyloxy)methyl]-7-[[4-[4-(pyrrolidinodithiocarbam-atemethyl)phenyl]butyryl]-amino]-8-oxo-5-thia-1-azabi-cyclo[4.2.0]oct-2-ene-2-carboxylic acid |
| 2-methyl-4-[p-(piperi-dinothiocarbamatemethyl)-phenyl]butyric acid | 3-[(acetyloxy)methyl]-7-[[4-[4-(piperidinodithiocarbam-atemethyl)phenyl]-2-methyl-butyryl]amino]-8-oxo-5-thia-1-azabicyclo[4.2.0]oct-2-ene-2-carboxylic acid |
| 2-hydroxy-4-[p-morpholino-dithiocarbamatemethyl)-phenyl]butyric acid | 3-[(acetyloxy)methyl]-7-[[4-[4-(morpholinodithiocarbam-atemethyl]phenyl]-2-hydroxy-butyryl]amino]-8-oxo-5-thia-1-azabicyclo[4.2.0]oct-2-ene-2-carboxylic acid |
| p-(monothiocarbamate-methyl)phenoxyacetic acid | 3-[(acetyloxy)methyl]-7-[[2-[4-(monothiocarbamatemethyl)-phenoxy]acetyl]amino]-8-oxo-5-thia-1-azabicyclo[4.2.0]-oct-2-ene-2-carboxylic acid |
| 2-[p-(N,N-dimethylmono-thiocarbamatemethyl)-phenoxy]propionic acid | 3-[(acetyloxy)methyl]-7-[[2-[4-(N,N-dimethylmonothiocar-bamatemethyl)phenoxy]-2-methylacetyl]amino]-8-oxo-5-thia-1-azabicyclo[4.2.0]-oct-2-ene-2-carboxylic acid |
| 4-[p-(N,N-diethylmono-thiocarbamatemethyl)-phenoxy]butyric acid | 3-[(acetyloxy)methyl]-7-[[4-[4-(N,N-diethylmonothiocar-bamatemethyl)phenoxy]butyryl]-amino[-8-oxo-5-thia-1-azabi-cyclo[4.2.0]oct-2-ene-2-carboxylic acid |
| 2-methyl-4-[p-(N,N-di-n-propyl-monothiocarbamatemethyl)phen-oxy]butyric acid | 3-[(acetyloxy)methyl]-7-[[4-[4-(N,N-di-n-propylmonothio-carbamatemethyl)phenoxy]-2-methylbutyryl] amino]-8-oxo-5-thia-1-azabicyclo[4.2.0]-oct-2-ene-2-carboxylic acid |
| 3-[p-(N,N-di-n-butylmonothio-carbamatemethyl)phenoxy]propi-onic acid | 3-[(acetyloxy)methyl]-7-[[3-[4-(N,N-di-n-butylmonothio-carbamatemethyl)phenoxy]-propionyl]amino]-8-oxo-5-thia-1-azabicyclo[4.2.0]-oct-2-ene-2-carboxylic acid |
| 3-[p-(pyrrolidinomonothiocar-bamatemethyl)phenoxy]lactic acid | 3-[(acetyloxy)methyl]-7-[[3-[4-(pyrrolidinomonothiocar-bamatemethyl)phenoxy]-2-hydroxypropionyl]amino]-8-oxo-5-thia-1-azabicyclo-[4.2.0]oct-2-ene-2-carboxylic acid |
| p-(piperidinomonothiocarbamate-methyl)anilinoacetic acid | 3-[(acetyloxy)methyl]-7-[[2-[4-(piperidinomonothiocar-bamtemethyl)anilino]acetyl]-amino]-8-oxo-5-thia-1-azabi-cyclo[4.2.0]oct-2-ene-2-carboxylic acid |
| 2-hydroxy-2-[5-(morpholinomono-thiocarbamatemethyl)-2-thi-enyl]acetic acid | 3-[(acetyloxy)methyl]-7-[[2-[5-(morpholinomonothiocar-bamatemethyl)-2-thienyl]-2-hydroxyacetyl]amino]-8-oxo-5-thia-1-azabicyclo[4.2.0]-oct-2-ene-2-carboxylic acid |
| 2-[p-(monothiocarbamatemethyl)-anilino]propionic acid | 3-[(acetyloxy)methyl]-7-[[2-[4-(monothiocarbamatemethyl)-anilino]-2-methylacetyl]am-ino]-8-oxo-5-thia-1-azabi- |

Table VI-continued

| ACID | CEPHALOSPORIN DERIVATIVE |
|---|---|
| | cyclo[4.2.0]oct-2-ene-2-carboxylic acid |
| 4-[p-(piperidinomonothiocarbamate)anilino]butyric acid | 3-[(acetyloxy)methyl]-7-[[4-[4-(piperidinomonothiocarbamate)anilino]butyryl]amino]-8-oxo-5-thia-1-azabicyclo[4.2.0]oct-2-ene-2-carboxylic acid |
| 3-[(p-pyrrolidinomonothiocarbamatemethyl)anilino butyric acid | 3-[(acetyloxy)methyl]-7-[[3-[4-(pyrrolidinomonothiocarbamatemethyl)anilino]-2-methylpropionyl]amino]-8-oxo-5-thia-1-azabicyclo-[4.2.0]oct-2-ene-2-carboxylic acid |
| p-(N,N-di-n-butylmonothiocarbamatemethyl)phenylthioacetic acid | 3-[(acetyloxy)methyl]-7-[[2-[4-(N,N-di-n-butylmonothiocarbamatemethyl)phenylthio]acetyl]amino]-8-oxo-5-thia-1-azabicyclo[4.2.0]oct-2-ene-2-carboxylic acid |
| 2-[p-(N,N-di-n-propylmonothiocarbamatemethyl)phenyl]thiopropionic acid | 3-[(acetyloxy)methyl]-7-[[2-[4-(N,N-di-n-propylmonothiocarbamatemethyl)phenylthio]-2-methylacetyl]amino]-8-oxo-5-thia-1-azabicyclo[4.2.0]-oct-2-ene-2-carboxylic acid |
| 4-[p-(N,N-diethylmonothiocarbamatemethyl)phenyl]thiobutyric acid | 3-[(acetyloxy)methyl]-7-[[4-[4-(N,N-diethylmonothiocarbamatemethyl)phenylthio]butyryl]amino]-8-oxo-5-thia-1-azabicyco[4.2.0]oct-2-ene-2-carboxylic acid |
| p-chloro-o-(N,N-dimethylmonothiocarbamatemethyl)phenylacetic acid | 3-[(acetyloxy)methyl]-7-[[2-[2-(chloro)-4-(N,N-dimethylmonothiocarbamatemethyl)-phenyl]acetyl]amino]-8-oxo-5-thia-1-azabicyclo[4.2.0]-oct-2-ene-2-carboxylic acid |

EXAMPLE 22

3-[(Acetyloxy)methyl]-7-[[2-[4-(monothiocarbamatemethyl)phenyl]-2-aminoacetyl]amino]-8-oxo-5-thia-1-azabicyclo[4.2.0]oct-2-ene-2-carboxylic acid p-(Monothiocarbamatemethyl)phenylglycine, obtained from the corresponding hydrochloride described hereinabove by treatment with base, wherein the amino group is protected with tert-butoxycarbonyl, is treated with isobutylchloroformate in the presence of triethylamine. Equimolar amounts of the thus obtained mixed anhydride and the triethylamine salt of 3-[(acetyloxy)methyl]-7-amino-8-oxo-5-thia-1-azabicyclo[4.2.0]oct-2-ene-2-carboxylic acid are reacted at 0° C for about 4 hours. The resulting product is isolated and the amine protecting group is removed by acid hydrolysis to give 3-[(acetyloxy)methyl]-7-[[2-[4-(monothiocarbamatemethyl)phenyl]-2-aminoacetyl]amino]-8-oxo-5-thia-1-azabicyclo[4.2.0]oct-2-ene-2-carboxylic acid.

When an appropriate amount of an amino acid listed in the following Table VII is substituted for p-(monothiocarbamatemethyl)phenylglycine in the above Example 22, the corresponding cephalosporin derivative listed in the following Table VII is obtained. The amino acids are obtained from the corresponding hydrochloride described hereinabove by treatment with base.

TABLE VII

| AMINO ACID | CEPHALOSPORIN DERIVATIVE |
|---|---|
| p-(morpholinodithiocarbamatemethyl)phenylalanine | 3-[(acetyloxy)methyl]-7-[[3-[4-(morpholinodithiocarbamatemethyl)phenyl]-2-aminopropionyl]amino]-8-oxo-5-thia-1-azabicyclo[4.2.0]-oct-2-ene-2-carboxylic acid |
| 2-amino-4-[p-(piperidinodithiocarbamatemethyl)phenyl]butyric acid | 3-[(acetyloxymethyl]-7-[[4-[4-(piperidinodithiocarbamatemethyl)phenyl]-2-aminobutyryl]amino]-8-oxo-5-thia-1-azabicyclo[4.2.0]oct-2-ene-2-carboxylic acid |
| 2-amino-4-[p-(pyrrolidinodithiocarbamatemethyl)phenoxy]-butyric acid | 3-[(acetyloxy)methyl]-7-[[4-[4-(pyrrolidinodithiocarbamatemethyl)phenoxy]-2-aminobutyryl]amino]-8-oxo-5-thia-1-azabicyclo[4.2.0]oct-2-ene-2-carboxylic acid |

TABLE VII-continued

| AMINO ACID | CEPHALOSPORIN DERIVATIVE |
| --- | --- |
| 3-[p-(N,N.-di-n-butyldithio-carbamatemethyl)phenoxy]alanine | 3-[(acetyloxy)methyl]-7-[[3-[4-(N,N-di-n-butyldithiocarbamatemethyl)phenoxy]-2-aminopropionyl]amino]-8-oxo-5-thia-1-azabicyclo[4.2.0]-oct-2-ene-2-carboxylic acid |
| 2-amino-4-[p-(N,N-di-n-propyldithiocarbamatemethyl)anilino]butyric acid | 3-[(acetyloxy)methyl]-7-[[4-[4-(N,N-di-n-propyldithiocarbamatemethyl)anilino]-2-aminobutyryl]amino]-8-oxo-5-thia-1-azabicyclo[4.2.0]-oct-2-ene-2-carboxylic acid |
| 2-amino-4-[p-(N,N-diethyldithiocarbamatemethyl)phenyl]thiobutyric acid | 3-[(acetyloxy)methyl]-7-[[4-[4-(N,N-diethyldithiocarbamatemethyl)phenylthio]-2-aminobutyryl]amino]-8-oxo-5-thia-1-azabicyclo[4.2.0]-oct-2-ene-2-carboxylic acid |
| 3-[p-(N,N-dimethyldithiocarbamatemethyl)phenyl]thioalanine | 3-[(acetyloxy)methyl]-7-[[3-[4-(N,N-dimethyldithiocarbamatemethyl)phenylthio]-2-aminopropionyl]amino]-8-oxo-5-thia-1-azabicyclo[4.2.0]-oct-2-ene-2-carboxylic acid |
| 2-[2-(5-dithiocarbamatemethyl)-thienyl]glycine | 3-[(acetyloxy)methyl]-7-[[2-[5-(dithiocarbamatemethyl)-2-thienyl]-2-aminoacetyl]-amino]-8-oxo-5-thia-1-azabicyclo[4.2.0]oct-2-ene-2-carboxylic acid |
| 2-amino-3-[2-(5-dithiocarbamatemethyl)thienyl]propionic acid | 3-[(acetyloxy)methyl]-7-[[3-[5-(dithiocarbamatemethyl)-2-thienyl]-2-aminopropionyl]-amino]-8-oxo-5-thia-1-azabicyclo[4.2.0]oct-2-ene-2-carboxylic acid |
| 2-amino-4-[2-(5-N,N-dimethyldithiocarbamate)thienyl]butyric acid | 3-[(acetyloxy)methyl]-7-[[4-[5-(N,N-dimethyldithiocarbamate)-2-thienyl]-2-aminobutyryl]amino]-8-oxo-5-thia-1-azabicyclo[4.2.0]oct-2-ene-2-carboxylic acid |

EXAMPLE 23

3-[(acetyloxy)methyl]-7-[[2-[4-(N,N-diethyldithiocarbamatemethyl)phenyl]-2-carboxyacetyl]amino]-8-oxo-5-thia-1-azabicyclo[4.2.0]oct-2-ene-2-carboxylic acid α-Carboxy-p-N,N-diethyldithiocarbamatemethylphenylacetylnitrophenyl polymer, prepared according to the procedure described in Canadian Pat. No. 892,580, carrying 4 m mole of p-N,N-diethyldithiocarbamatemethylphenylmalonic acid was suspended for 8 hours and 20 ml of dry ethylene chloride solution containing 1 m mole of 3-[(acetyloxy)methyl]-7-amino-8-oxo-5-thia-1-azabicyclo[4.2.0]oct-2-ene-2-carboxylic acid triethylammonium salt, which is prepared from 544 mg of 7-aminocephalosporanic acid (1 m mole) in 0.56 ml of triethylamine (1 m mole) at room temperature. After only traces of 7-aminocephalosporanic acid remain in solution which is determined by thin layer chromatography on cellulose and 70% aqueous propanol, the polymer was filtered off and washed with 3 portions of 50 ml each of methylene chloride. The combined filtrates were evaporated and the residue was dissolved in 20 ml of distilled water. This solution was acidified to pH 2 by adding 0.2 normal hydrochloric acid and extracted with ethylacetate. The organic solution was dried over sodium sulfate and evaporated at room temperature. The remaining solid was dried overnight over phosphorous pentoxide under vacuum to give 3-[(acetyloxy)methyl]-7-[[2-[4-(N,N-diethyldithiocarbamatemethyl)phenyl]-2-carboxyacetyl]amino]-8-oxo-5-thia-1-azabicyclo[4.2.0]oct-2-ene-2-carboxylic acid. When in the procedure of Example 23 an appropriate amount of an acid listed in the following Table VIII is substituted for p-(N,N-diethyldithiocarbamatemethyl)phenylmalonic acid the respective cephalosporin derivatives listed in the following Table VIII are obtained.

TABLE VIII

| ACID | CEPHALOSPORIN DERIVATIVE |
| --- | --- |
| 2-sulfo-p-(N,N-di-n-propylthiocarbamatemethyl)phenylacetic acid | 3-[(acetyloxy)methyl]-7-[[2-[4-(N,N-di-n-propyldithiocarbamatemethyl)phenyl]-2-sulfoacetyl]amino]-8-oxo-5-thia-1-azabicyclo[4.2.0]-oct-2-ene-2-carboxylic acid |
| 3-[p-(N,N-di-n-butyldithiocarbamatemethyl)phenyl]-2- | 3[(acetyloxy)methyl]-7-[[3-[4-(N,N-di-n-butyldithiocar- |

TABLE VIII-continued

| ACID | CEPHALOSPORIN DERIVATIVE |
| --- | --- |
| sulfopropionic acid | bamatemethyl)phenyl]-2-sulfopropionyl]amino]-8-oxo-5-thia-1-azabicyclo[4.2.0]-oct-2-ene-2-carboxylic acid |
| 4-[p-(pyrrolidinodithio-carbamatemethyl)phenyl]-2-sulfobutyric acid | 3-[(acetyloxy)methyl]-7-[[4-[4-(pyrrolidinodithiocarbamatemethyl)phenyl]-2-sulfoburyryl]amino]-8-oxo-5-thia-1-azabicyclo[4.2.0]oct-2-ene-2-carboxylic acid |
| p-(piperidinodithiocarbamatemethyl)benzylmalonic acid | 3-[(acetyloxy)methyl]-7-[[3-[4-(piperidinodithiocarbamatemethyl)phenyl]-2-carboxypropionyl]amino]-8-oxo-5-thia-1-azabicyclo[4.2.0]-oct-2-ene-2-carboxylic acid |
| p-(morpholinodithiocarbamatemethyl)phenethylmalonic acid | 3-[(acetyloxy)methyl]-7-[[4-[4-(morpholinodithiocarbamatemethyl)phenyl]-2-carboxybutyryl]amino]-8-oxo-5-thia-1-azabicyclo[4.2.0]oct-2-ene-2-carboxylic acid |
| 2-[p-(monothiocarbamatemethyl)-phenoxy]ethylmalonic acid | 3-[(acetyloxy)methyl]-7-[[4-[4-(monothiocarbamatemethyl)-phenoxy]2-carboxybutyryl]-amino]-8-oxo-5-thia-1-azabicyclo[4.2.0]oct-2-ene-2-carboxylic acid |
| 2-[p(N,N-dimethylmonothiocarbamatemethyl)phenyl]thioethylmalonic acid | 3-[(acetyloxy)methyl]-7-[[4-[4-(N,N-dimethylmonothiocarbamatemethyl)phenylthio]-2-carboxybutyryl]amino]-8-oxo-5-thia-1-azabicyclo[4.2.0]-oct-2-ene-2-carboxylic acid |
| p-(N,N-diethylmonothiocarbamatemethyl)anilinomethylmalonic acid | 3-[(acetyloxy)methyl]-7-[[3-[4-(N,N-diethylmonothiocarbamatemethyl)anilino]-2-carboxypropionyl]amino]-8-oxo-5-thia-1-azabicyclo[4.2.0]-oct-2-ene-2-carboxylic acid |
| 2-[5-(N,N-di-n-propylmonothiocarbamatemethyl)-2-thienyl]-malonic acid | 3-[(acetyloxy)methyl]-7-[[2-[5-(N,N-di-n-propylmonothiocarbamatemethyl)-2-thienyl]-2-carboxyacetyl]-amino]-8-oxo-5-thia-1-azabicyclo[4.2.0]oct-2-ene-2-carboxylic acid |
| 2-[5-(N,N-di-n-butylmonothiocarbamatemethyl)-2-thienyl]-malonic acid | 2-[(acetyloxy)methyl]-7-[[3-[5-(N,N-di-n-butylmonothiocarbamatemethyl)-2-thienyl]-2-carboxypropionyl]amino]-8-oxo-5-thia-1-azabicyclo-[4.2.0]oct-2-ene-2-carboxylic acid |

When by the general procedure of Example 18 appropriate amounts of an acid and a 7-aminocephalosporanic acid derivative listed in the following Table IX are reacted the corresponding cephalosporin product listed in Table IX are obtained.

TABLE IX

| ACID | 7-AMINOCEPHALOSPORANIC ACID DERIVATIVE | CEPHALOSPORIN PRODUCT |
| --- | --- | --- |
| p-(N,N-di-n-propyldithio-carbamatemethyl)phenylacetic acid | 3-[(acetyloxy)methyl]-7-amino-7-methoxy-8-oxo-5-thia-1-azabicyclo-[4.2.0]oct-2-ene-2-carboxylic acid | 3-[(acetyloxy)methyl]-7-[[2-[4-(N,N-di-n-propyl-dithiocarbamatemethyl-phenyl]acetyl]amino]-7-methoxy-8-oxo-5-thia-1-azabicyclo[4.2.0]cot-2-ene-2-carboxylic acid |
| p-(dithiocarbamatemethyl)-phenylacetic acid | 3-[(2-methyl-1,3,4-thiadiazol-5-ylthio)methyl]-7-amino-7-methoxy-8-oxo-5-thia-1-azabicyclo[4.2.0]-oct-2-ene-2-carboxylic acid | 7-[[2-[4-(dithiocarbamatemethyl)phenyl]acetyl]-amino]-7-methoxy-3-[(2-methyl-1,3,4-thiadiazol-5-ylthio)methyl]-8-oxo-5-thia-1-azabicyclo[4.2.0]-oct-2-ene-2-carboxylic acid |
| p-(N,N-diethyldithiocarbamatemethyl)phenylacetic acid | 3-[(1-methyltetrazol-5-ylthio)-methyl]-7-amino-8-oxo-5-thia-1- | 7-[[2-[4-(N,N-diethyldithiocarbamatemethyl)phe- |

TABLE IX-continued

| ACID | 7-AMINOCEPHALOSPORANIC ACID DERIVATIVE | CEPHALOSPORIN PRODUCT |
| --- | --- | --- |
| | azabicyclo[4.2.0]oct-2-ene-2-carboxylic acid p-pivalyloxybenzyl ester | nyl]acetyl]amino]-3-[(1-methyltetrazol-5-ylthio)-methyl]-8-oxo-5-thia-1-azabicyclo[4.2.0]oct-2-ene-2-carboxylic acid |
| p-(morpholinodithiocarbamate-methyl)phenylacetic acid | 3-[(2-methyl-1,3,4-oxadiazol-5-ylthio)methyl]-7-amino-8-oxo-5-thia-1-azabicyclo[4.2.0]oct-2-ene-2-carboxylic acid 2-amino-3-methylbutyryloxymethyl ester | 7-[[2-[4-(morpholinodithiocarbamatemethyl)phenyl]acetyl]amino]-3-[(2-methyl-1,3,4-oxadiazol-5-ylthio)methyl]-8-oxo-5-thia-1-azabicyclo[4.2.0]-oct-2-ene-2-carboxylic acid |
| p-(monothiocarbamatemethyl)-phenylacetic acid | 3-[(1-methyltetrazol-5-ylthio)methyl]-7-amino-8-oxo-5-thia-1-azabicyclo[4.2.0]-oct-2-ene-2-carboxylic acid pivalyloxymethyl ester | 7-[[2-[4-monothiocarbamatemethyl)phenyl]acetyl]-amino]-3-[(1-methyltetrazol-5-ylthio)methyl]-8-oxo-5-thia-1-azabicyclo-[4.2.0]oct-2-ene-2-carboxylic acid pivalyloxymethyl ester |
| p-(piperidinomonothiocarbamatemethyl)phenylacetic acid | 3-[2-methyl-1,3,4-thiadiazol-5-ylthio)-methyl]-7-amino-8-oxo-5-thia-1-azabicyclo[4.2.0]oct-2-ene-2-carboxylic | 7-[[2-[4-(piperidinomonothiocarbamatemethyl)phenyl]-acetyl]amino]-3-[[2-methyl-1-3,4,-thiadiazol-5-ylthio)-methyl]-8-oxo-5-thia-1-azabicyclo[4.2.0]oct-2-ene-2-carboxylic acid |
| o-chloro-p-(N,N-dimethyl-monothiocarbamatemethyl)-phenylacetic aicd | 3-[(acetyloxy)methyl]-7-amino-8-oxo-5-thia-1-azabicyclo[4.2.0]oct-2-ene-2-carboxylic acid p-pivalyloxybenzyl ester | 3-[(acetyloxy)methyl]-7-[[2-[2-(chloro)-4-(N,N-dimethylmonothiocarbamatemethyl)phenyl]acetyl]amino]-8-oxo-5-thia-1-azabicyclo-[4.2.0]oct-2-ene-2-carboxylic acid p-pivalyloxybenzyl ester |
| 4-[p-(N,N-diethylmonothiocarbamatemethyl)phenyl]thiobutyric acid | 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 3-[(acetyloxy)methyl]-7-[[4-[4-(N,N-diethylmonothiocarbamatemethyl)phenyl]butyryl]amino]-8-oxo-5-thia-1-azabicyclo[4.2.0]oct-2-ene-2-carboxylic acid N-ethoxycarbonyl-N-methylaminomethyl ester |
| 2-[p-(monothiocarbamatemethyl)anilino]propionic acid | 3-[(acetyloxy)methyl]-7-amino-8-oxo-5-thia-1-azabicyclo[4.2.0]oct-2-ene-2-carboxylic acid 2-amino-3-methylbutyryloxymethyl ester | 3-[(acetyloxy)methyl]-7-[[3-[4-(monothiocarbamatemethyl)anilino]propionyl]-amino]-8-oxo-5-thia-1-azabicyclo[4.2.0]oct-2-ene-2-carboxylic acid 2-amino-3-methylbutyryloxymethyl ester |
| 2-hydroxy-2-[5-(morpholino-monothiocarbamatemethyl)-2-thienyl]acetic aicd | 3-[(acetyloxy)methyl]-7-amino-8-oxo-5-thia-1-azabicyclo[4.2.0]oct-2-ene-2-carboxylic acid pivalyloxymethyl ester | 3-[(acetyloxy)methyl]-7-[[2-[5-(morpholinomonothiocarbamatemethyl)-2-thienyl]-2-hydroxyacetyl]amino]-8-oxo-5-thia-1-azabicyclo-[4.2.0]oct-2-ene-2-carboxylic acid pivalyloxymethyl ester |
| p-(monothiocarbamatemethyl)-phenoxyacetic acid | 3-[1-methyltetrazol-5-ylthio)methyl]-7-amino-8-oxo-5-thia-1-azabicyclo[4.2.0]oct-2-ene-2-carboxylic acid | 7-[[2-[4-(monothiocarbamatemethyl)phenoxy]acetyl]-amino]-3-[1-methyltetrazol-5-ylthio)methyl]-8-oxo-5-thia-1-azabicyclo[4.2.0]-oct-2-ene-2-carboxylic acid |
| p-(dithiocarbamatemethyl)-hydrotropic acid | 3-[(tetrazol-5-ylthio)methyl]-7-amino-8-oxo-5-thia -1-azabicyclo[4.2.0]oct-2-ene-2-carboxylic acid | 7-[[2-[4-(monothiocarbamatemethyl)phenyl]-2-methylacetyl]amino]-3-[(tetrazol-5-ylthio)methyl]-8-oxo-5-thia-1-azabicyclo[4.2.0]-oct-2-ene-2-carboxylic acid |
| p-(monothiocarbamatemethyl)-phenylacetic acid | 3-methyl-7-amino-8-oxo-5-thia-1-azabicyclo[4.2.0]oct-2-ene-2-carboxylic acid | 3-methyl-7-[[2-[4-(monothiocarbamatemethyl)-phenyl]acetyl]amino]-8-oxo-5-thia-1-azabicyclo[4.2.0]oct-2-ene-2-carboxylic acid |

By the general procedure of Example 22 reaction of appropriate amounts of an amine protected acid and a cephalosporin derivative listed in the following Table X

| ACID | 7-AMINOCEPHALOSPORIN DERIVATIVE | CEPHALOSPORIN PRODUCT |
|---|---|---|
| 3-[p-(morpholinodithiocar-bamatemethyl)phenyl]alanine | 3-[(acetoxy)methyl]-7-amino-8-oxo-5-thia-1-azabicyclo[4.2.0]oct-2-ene-2-carboxylic acid pivalyloxymethyl ester | 3-[(acetyloxyl)methyl]-7-[[3-[4-(morpholinodithiocarbamate-methyl)phenyl]propionyl]amino]-8-oxo-5-thia-1-azabicyclo[4.2.0]-oct-2-ene-2-carboxylic acid pivalyloxymethyl ester |
| 2-amino-4-[p-(pyrrolidino-thiocarbamatemethyl)phenoxy]-butyric acid | 3-[(acetyloxy)methyl]-7-amino-8-oxo-5-thia-1-azabicyclo[4.2.0]oct-2-ene-2-carboxylic acid N-methyl-N-propionylaminomethyl ester | 3-[(acetyloxy)methyl]-7-[[4-[4-(pyrrolidinodithiocarbamate-methyl)phenoxy]-2-amino-butyryl]-amino]-8-oxo-5-thia-1-azabicyclo-[4.2.0]oct-2-ene-2-carboxylic acid N-methyl-N-propionylaminoethyl ester |
| 2-amino-4-(p-N,N-di-n-propyl-dithiocarbamatemethyl)anilino] butyric aicd | 3-[(2-methyl1-1,3,4-thiadiazol-5-ylthio)methyl]-7-amino-8-oxo-5-thia-1-azabicyclo]4.2.0]oct-2-ene-2-carboxylic acid | 7-[[4-[4-(N,N-di-n-propyldithio-carbamatemethyl)anilino]-2-amino-butyryl]amino]-3-[(2-methyl-1,3,4-thiadiazol-5-ylthio)methyl]-8-oxo-5-thia-1-azabicyclo[4.2.0]oct-2-ene-2-carboxylic acid |
| 3-[p-(N,N-dimethyldithiocar-bamatemethyl)phenyl]thioala-nine | 3-[(acetyloxy)methyl]-7-amino-7-methoxy-8-oxo-5-thia-1-azabicyclo-[4.2.0]oct-2-ene-2-carboxylic aicd | 3-[(acetyloxy)methyl]-7-[[3-[4-(N,N-dimethyldithiocarbamate-methyl)phenylthio]-2-aminopro-pionyl]amino]-7-methoxyl-8-oxo-5-thia-1-azabicyclo[4.2.0]oct-2-ene-2-carboxylic acid |
| 2-amino-3-[5-(dithiocarbam-atemethyl)-2-thienyl]propi-onic acid | 3-[(tetrazol-5-ylthio)methyl]-7-amino] -8-oxo-5-thia-1-azabicyclo-[4.2.0]oct-2-ene-2-carboxylic acid p-pivalyloxybenzyl ester | 7-[[3-[5-(dithiocarbamate-methyl)-2-thienyl]-2-amino-propionyl]amino]-3-[(tetra-zol-5-ylthio)methyl]-8-oxo-5-thia-1-azabicyclo[4.2.0]-oct-2-ene-2-carboxylic acid p-(acetyloxy)benzyl ester |
| p-(monothiocarbamatemethyl)-phenylglycine | 3-[(1-methyltetrazol-5-ylthio)methyl]-7-amino-8-oxo-5-thia-1-azabicyclo-[4.2.0]oct-2-ene-2-carboxylic acid | 7-[[2-[4-(monothiocarbamate-methyl)phenyl]-2-aminoacetyl]-amino]-3-[1-methyltetrazol-5-ylthio)methyl]-8-oxo-5-thia--azabicyclo[4.2.0]oct-2-ene-2-carboxylic acid |
| p-(dithiocarbamatemethyl)-phenylglycine | 3-methyl-7-amino-8-oxo-5-thia-1-aza-bicyclo[4.2.0]oct-2-ene-2-carboxylic acid | 3-methyl-7-[[2-[4-(dithiocar-bamatemethyl)phenyl]-2-amino-acetyl]-8-oxo-5-thia-1-aza-bicyclo[4.2.0]oct-2-ene-2-carboxylic acid |
| p-(dithiocarbamatemethyl)-phenylglycine | 3-methyl-7-amino-7-methoxy-8-oxo-5-thia-1-azabicyclo[4.2.0]oct-2-ene-2-carboxylic acid pivalyloxy-methyl ester | 3-methyl-7-[[2-[4-(dithio-carbamatemethyl)phenyl]-2-aminoacetyl]amino-8-oxo-5-thia-1-azabicyclo[4.2.0]oct-2-ene-2-carboxylic acid pivalyloxymethyl ester |

By the general procedure of Example 23 reaction of appropriate amounts of an acid derivative and a 7-aminocephalosporin derivative listed in the following Table XI gives the corresponding cephalosporin product listed in the following Table XI.

TABLE XI

| ACID DERIVATIVE | 7-AMINOCEPHALOSPORIN DERIVATIVE | CEPHALOSPORIN PRODUCT |
|---|---|---|
| 2-sulfo-p-(N,N-di-n-propyl-dithiocarbamatemethyl)phenyl-acetic acid | 3-[(acetyloxy)methyl]-7-amino-8-oxo-5-thia-1-azabicyclo]4.2.0]oct-2-ene-2-carboxylic acid propionyloxymethyl ester | 3-[(acetyloxy)methyl]-7-[[2-[4-(N,N-di-n-propyldithiocar-bamatemethyl)phenyl]-2-sulfo-acetyl]amino]-8-oxo-5-thia-1-azabicyclo[4.2.0]oct-2-ene-2-carboxylic acid propionyloxy-methyl ester |
| p-(piperidinodithiocarbamate-methyl)benzylmalonic acid | 3-[(acetyloxy)methyl[-7-amino-8-oxo-5-thia-1-azabicyclo[4.2.0]oct-2-ene-2-carboxylic acid N-acetylaminomethyl-ester | 3-[(acetyloxy)methyl]-7-[[3-[4-(piperidinodithiocarbamate-methyl)phenyl]-2-carboxypro-pionyl]amino]-8-oxo-5-thia-1-azabicyclo[4.2.0]oct-2-ene-2-carboxylic acid N-acetylamino-methyl ester |
| 2-[p-(monothiocarbamatemethyl)-phenoxy]ethylmalonic acid | 3-[(acetyloxy)methyl]-7-amino-8-oxo 5-thia-1-azabicyclo[4.2.0]oct-2-ene-2-carboxylic acid p-(valaryloxy)ben-zyl ester | 3-[(acetyloxy)methyl]-7-[[4-[4-(monothiocarbamatemethyl)-phenoxy]-2-carboxybutyrl]-amino]-8-oxo-5-thia-1-azabi-cyclo[4.2.0]oct-2-ene-2-car-boxylic acid p-(valaryloxy)-benzyl ester |
| p-(N,N-diethylmonothiocarbam- | 3-[(1-methyltetrazol-5-ylthiomethyl]- | 7-[[3-[4-(N,N-diethylmonothio- |

TABLE XI-continued

| ACID DERIVATIVE | 7-AMINOCEPHALOSPORIN DERIVATIVE | CEPHALOSPORIN PRODUCT |
|---|---|---|
| atemethyl)anilinomethylmalonic acid | 7-amino-8-oxo-5-thia-1-azabicyclo[4.2.0]oct-2-ene-2-carboxylic acid | carbamatemethyl)anilino]-2-carboxypropionyl]amino]-3-[(1-methyltetrazol-5-ylthio)methyl]-8-oxo-5-thia-1-azabicyclo[4.2.0]oct-2-ene-2-carboxylic acid |
| p-(N,N-diethyldithiocarbamatemethyl)phenylmalonic acid | 3-[(acetyloxy)methyl]-7-amino-7-methoxy-8-oxo-5-thia-1-azabicyclo[4.2.0]oct-2-ene-2-carboxylic acid | 3-[(acetyloxy)methyl]-7-[[2-[4-(N,N-diethyldithiocarbamatemethyl)phenyl]-2-carboxyacetyl]amino]-7-methoxy-8-oxo-5-thia-1-azabicyclo[4.2.0]oct-2-ene-2-carboxylic acid |
| 2-[5-(N,N-di-n-butylmonothiocarbamatemethyl)-2-thienyl]malonic acid | 3-[3-methyl-1,2,4-thiadiazol-5-ylthio)methyl]-7-amino-8-oxo-5-thia-1-azabicyclo[4.2.0.]oct-2-ene-2-carboxylic acid propionyloxymethyl ester | 7-[[3-[5-(N,N-di-n-butylmono-0010 50 2-carboxypropionyl)amino]-3-[(3-methyl-1,2,4-thiadiazol-5-ylthio)methyl]-8-oxo-5-thia-1-azabicyclo[4.2.0]oct-2-ene-2-carboxylic acid propionyloxymethyl ester |
| p-(N,N-diethyldithiocarbamatemethyl)phenylmalonic acid | 3-methyl-7-amino-8-oxo-5-thia-1-azabicyclo[4.2.0]oct-2-ene-2-carboxylic acid | 3-methyl-7-[[2-[4-(N,N-diethyldithiocarbamatemethyl)phenyl]-2-carboxyacetyl]amino]-8-oxo-5-thia-1-azabicyclo[4.2.0]oct-2-ene-2-carboxylic acid |
| 2-[p-(monothiocarbamatemethyl)phenoxy]ethylmalonic acid | 3-[(acetyloxy)methyl]-7-amino-7-methoxy-8-oxo-5-thia-1-azabicyclo[4.2.0]oct-2-ene-2-carboxylic acid | 3-[(acetyloxy)methyl]-7-[[2-[4-(monothiocarbamatemethyl)phenoxy]-2-carboxyacetyl]amino]-8-oxo-5-thia-1-azabicyclo[4.2.0]oct-2-ene-2-carboxylic acid |

3-[(Acetyloxy)methyl]-7-[[2-[4-(dithiocarbamatemethyl)phenyl]acetyl]amino]-8-oxo-5-thia-1-azabicyclo[4.2.0]oct-2-ene-2-carboxylic acid A. A mixture of 1 g of 3-[(acetyloxy)methyl]-7-amino-8-oxo-5-thia-1-azabicyclo[4.2.0]oct-2-ene-2-carboxylic acid and 1 g of p-chloromethylphenylacetyl chloride in 45 ml of ethylacetate is refluxed for about 2 hours after which the solvent is removed under vacuum yielding a yellow-brown amorphous product which is chromatographed on silica gel using benzene-acetone as the eluant to give 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid. M.P. 164°–165° C. (dec.).

B. A mixture of 1.09 g (2.5 m mole) of 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid and 2.2 g (20 m mole) of ammonium dithiocarbamate in 40 ml of methanol was stirred under nitrogen atmosphere for 5 hours after which the solvent was evaporated and 30 ml of cold water and 60 ml of ethylacetate were added. The mixture was acidified with 10% aqueous hydrochloric acid to a pH of 2. The organic layer was washed with water until the water became neutral and was then dried over magnesium sulfate and evaporated. The residue was washed with ether and recrystallized from ethylacetate to give 3-[(acetyloxy)methyl]-7-[[2-[4-(dithiocarbamatemethyl)phenyl]acetyl]amino]-8-oxo-5-thia-1-azabicyclo[4.2.0]oct-2-ene-2-carboxylic acid.

In a similar manner other compounds of the invention may be prepared by coupling an appropriate halomethyl substituted acid listed in Table I, Table II, Table III and Examples 2, 3, 4, 6, and 7 with appropriate 7-aminocephalosporin derivatives as disclosed herein followed by reaction with a carbamate or salt thereof as described herein having the structure

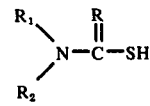

wherein R, $R_1$ and $R_2$ have the meanings defined in general Formula I.

EXAMPLE 25

3-[(Acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid N-ethoxycarbonyl-N-methylaminomethyl ester A mixture of 1.2 g of the sodium salt of 3-[(acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid and 0.5 g of N-chloromethyl-N-methylurethane in 40 ml of dimethylformamide is stirred at room temperature for 2 hours. The mixture is poured into ice-water and decanted. The oily residue is taken up in 75 ml of ethyl acetate and washed with 5 ml of dilute aqueous sodium bicarbonate and 15 ml of water then dried over magnesium sulfate, filtered and evaporated to give 3-[(acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid N-ethoxycarbonyl-N-methylaminoethyl ester.

EXAMPLE 26

3-[(Acetyloxy)methyl]-7-[[2-[4-(morpholinodithiocarbamatemethyl)phenyl]acetyl]amino]-8-oxo-5-thia-1-azabicyclo[4.2.0]oct-2-ene-2-carboxylic acid p-pivalyloxybenzyl ester To a solution of 1.8 g of 3-[(acetyloxy)methyl]-7-[[2-[4-(morpholinodithiocarbamatemethyl)phenyl]acetyl]amino]-8-oxo-5-thia-1-azabicyclo[4.2.0]oct-2-ene-2-carboxylic acid hydrochloride in 25 ml of dimethylformamide is added .78 g of p-pivalyloxybenzyl alcohol followed by cooling to 0° C after which 3.7 mole of dicyclohexylcarbodiimide in 7.5 ml of dimethylformamide is added dropwise with stirring. The reaction mixture is stirred for 1 hour at 0° C and for an additional 4 hours at room temperature. The formed dicyclohexylurea is removed by filtration. The filtrate is diluted with chloroform and washed with water. The organic layer is then dried over magnesium sulfate, filtered, and evaporated in vacuo to give an oil which is triturated with ether to give 3-[(acetyloxy)methyl]-7-[[2-[4-morpholinodithiocarbamatemethyl)phenyl]acetyl]amino]-8-oxo-5-thia-1-azabicyclo[4.2.0]oct-2-ene-2-carboxylic acid p-pivalyloxybenzyl ester.

EXAMPLE 27

3-[(Acetyloxy)methyl]-7-[[2-[4-(morpholinomonothiocarbamatemethyl)phenyl]-2-(5-indanyloxycarbonyl)acetyl]amino]-8-oxo-5-thia-1-azabicyclo[4.2.0]oct-2-ene-2-carboxylic acid To 25.3 m mole of 3-[(acetyloxy)methyl]-7-[[2-[4-morpholinomonothiocarbamatemethyl)phenyl]-2-carboxyacetyl]amino]-8-oxo-5-thia-1-azabicyclo[4.2.0]oct-2-ene-2-carboxylic acid in 35 ml dioxane is added 6N hydrochloric acid to give a pH of 2.5. Then 24.1 m moles N,N'-dicyclohexylcarbodiimide in 35 ml dioxane is added and the mixture is stirred at room temperature for 15 to 20 minutes followed by the addition of 24.1 m moles of 5-indanol. The mixture is stirred for 4 hours. The formed N,N'-dicyclohexylurea is removed by filtration and the filtrate is extracted 3 times with methyl isobutyl ketone. The organic extract is washed with water, dried over magnesium sulfate and concentrated to dryness in vacuo to yield 3-[(acetyloxy)methyl]-7-[[2-[4-(morpholinomonothiocarbamatemethyl)phenyl]-2-(5-indanyloxycarbonyl)acetyl]amino]-8-oxo-5-thia-1-azabicyclo[4.2.0]oct-2-ene-2-carboxylic acid.

EXAMPLE 28

3-[(2-Methyl-1,3,4-thiadiazol-5-ylthio)methyl]-7-[[2-[4-(dithiocarbamatemethyl)phenyl]acetyl]amino]-8-oxo-5-thia-1-azabicyclo[4.2.0]oct-2-ene-2-carboxylic acid A solution of 3 mM of 3-[(acetyloxy)methyl]-7-[[2-[4-(dithiocarbamatemethyl)phenyl]acetyl]amino]-8-oxo-5-thia-1-azabicyclo[4.2.0]oct-2-ene-2-carboxylic acid in 100 ml of water is treated with 3 mM of sodium bicarbonate and 6 mM of 2-methyl-1,3,4-thiadiazol-5-ylthio at 70° C under nitrogen for 3½ hours. The water is removed in vacuo and the residue is taken up in methanol. A large excess of acetonitrile is added to precipitate the product which is isolated by filtration and dried in a vacuum desiccator to give 3-[(2-methyl-1,3,4-thiadiazol-5-ylthio)methyl]-7-[[2-[4-(dithiocarbamatemethyl)phenyl]acetyl]amino]-8-oxo-5-thia-1-azabicyclo[4.2.0]oct-2-ene-2-carboxylic acid.

Similarly, other compounds of the invention wherein the 3-position of the cephalosporin ring is substituted with a heterocyclicthiomethyl group may be prepared from the corresponding 3-[(acetyloxy)methyl]-substituted cephalosporin compound by reaction with an appropriate heterocyclicthiol derivative as described herein.

We claim:

1. A compound selected from a base of the formula:

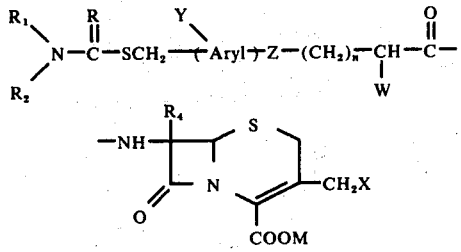

wherein each of $R_1$ and $R_2$ is selected from hydrogen and lower alkyl of from 1 to 4 carbon atoms or $NR_1R_2$ taken together form a monocyclic heterocyclic group selected from pyrrolidino, piperidino and morpholino; R is oxygen or sulfur; Aryl is selected from phenyl and 2-thienyl; Y is selected from hydrogen, chlorine, bromine, a straight or branched lower alkyl group of from 1 to 4 carbon atoms and a lower alkoxy group of from 1 to 4 carbon atoms with the proviso that when Aryl is 2-thienyl, Y is hydrogen; Z is selected from a bond, oxygen, sulfur and imino with the proviso that when Aryl is 2-thienyl, Z is a bond; W is selected from hydrogen, methyl, amino, hydroxy, $SO_3H$ and $COOR_3$ wherein $R_3$ is selected from hydrogen and 5-indanyl; n is zero, 1 or 2 with the proviso that when W is other than hydrogen or methyl and Z is other than a bond, n is not zero; $R_4$ is selected from hydrogen and methoxy; M is selected from hydrogen; a pharmaceutically acceptable nontoxic cation; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen atom may be substituted with an alkyl group of from 1 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms and the amino nitrogen may be mono- or di-substituted with a lower alkyl group of from 1 to 4 carbon atoms; X is hydrogen or acetoxy; and pharmaceutically acceptable salts thereof.

2. A compound of claim 1 wherein Aryl is phenyl.

3. A compound of claim 2 wherein $R_4$ is in the cis-position.

4. A compound of claim 1 wherein Aryl is 2-thienyl.

5. A compound of claim 4 wherein $R_4$ is in the cis-position.

6. A compound of claim 1 wherein W is hydrogen.

7. A compound of claim 6 wherein Z is a bond.
8. A compound of claim 6 wherein Z is oxygen or sulfur.
9. A compound of claim 6 wherein Z is imino.
10. A compound of claim 1 wherein W is methyl.
11. A compound of claim 10 wherein Z is a bond.
12. A compound of claim 10 wherein Z is oxygen or sulfur.
13. A compound of claim 10 wherein Z is imino.
14. A compound of claim 1 wherein W is hydroxy.
15. A compound of claim 14 wherein Z is a bond.
16. A compound of claim 14 wherein Z is oxygen or sulfur.
17. A compound of claim 14 wherein Z is imino.
18. A compound of claim 1 wherein W is amino.
19. A compound of claim 18 wherein Z is a bond.
20. A compound of claim 18 wherein Z is oxygen or sulfur.
21. A compound of claim 18 wherein Z is imino.
22. A compound of claim 1 wherein W is $COOR_3$ or $SO_3H$.
23. A compound of claim 22 wherein Z is a bond.
24. A compound of claim 22 wherein Z is oxygen or sulfur.
25. A compound of claim 22 wherein Z is imino.
26. A compound selected from a base of the formula:

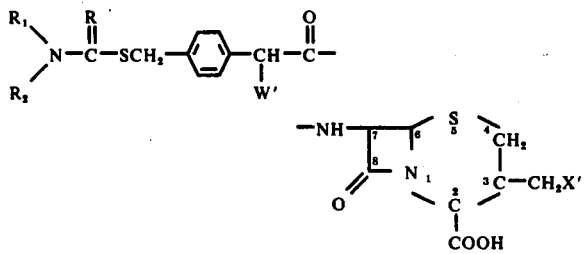

wherein R is oxygen or sulfur; each of $R_1$ and $R_2$ is selected from hydrogen and lower alkyl of from 1 to 4 carbon atoms or $NR_1R_2$ taken together is selected from a monocyclic heterocyclic group selected from pyrrolidino, piperidino and morpholino; W' is selected from hydrogen, hydroxy, amino, COOH and $SO_3H$; X' is hydrogen or acetoxy; and wherein the hydrogen atoms at the 6- and 7-positions are cis to one another; and pharmaceutically acceptable salts thereof.

27. A compound of claim 26 wherein X' is acetoxy.
28. A compound of claim 27 which is 3-[(acetyloxy)methyl]-7-[[2-[4-(N,N-diethyldithiocarbamatemethyl)phenyl]acetyl]amino]-8-oxo-5-thia-1-azabicyclo[4.2.0]oct-2-ene-2-carboxylic acid and pharmaceutically acceptable salts thereof.
29. A compound of claim 27 which is 3-[(acetyloxy)methyl]-7-[[2-[4-(dithiocarbamatemethyl)phenyl]-2-hydroxyacetyl]amino]-8-oxo-5-thia-1-azabicyclo[4.2.0]oct-2-ene-2-carboxylic acid and pharmaceutically acceptable salts thereof.
30. A compound of claim 27 which is 3-[(acetyloxy)methyl]-7-[[2-[4-(morpholinodithiocarbamatemethyl)phenyl]-2-aminoacetyl]amino]-8-oxo-5-thia-1-azabicyclo[4.2.0]oct-2-ene-2-carboxylic acid and pharmaceutically acceptable salts thereof.
31. A compound of claim 27 which is 3-[(acetyloxy)methyl]-7-[[2-[4-(morpholinomonothiocarbamatemethyl)phenyl]-2-carboxyacetyl]amino]-8-oxo-5-thia-1-azabicyclo[4.2.0]oct-2-ene-2-carboxylic acid and pharmaceutically acceptable salts. thereof.
32. A compound of claim 26 which is 3-methyl-7-[[2-[4-(dithiocarbamatemethyl)phenyl]-2-aminoacetyl]amino]-8-oxo-5-thia-1-azabicyclo[4.2.0]oct-2-ene-2-carboxylic acid and pharmaceutically acceptable salts thereof.

* * * * *

UNITED STATES PATENT OFFICE
CERTIFICATE OF CORRECTION

PATENT NO. : 4,031,083
DATED : February 16, 1978
INVENTOR(S) : F. Haviv, A. Patchornik and J. Altman It is certified that error appears in the above-identified patent and that said Letters Patent are hereby corrected as shown below:

Column 2, line 25, that portion of the formula reading  $-CH_2O-\overset{O}{\underset{\|}{C}}R_5$ should read $-CH_2-O-\overset{O}{\underset{\|}{C}}R_5$. Column 5, line 1 ...of the compound... should read --of the compounds--; line 42 ...too make... should read --to make--. Column 7, line 52 ...from 50 to C c... should read --from 50 to 80°C--. Column 9, line 22 ...aciid... should read --acid--. Column 10, line 15 ...$R_3$ in 5-indanyl... should read --$R_3$ is 5-indanyl--; line 18 ...lat a pH of... should read --at a pH of--. Column 18, line 32 ...When the procedure... should read --When in the procedure--. Table IV, 1st listing, 1st Column ...3-[acetyloxy)... should read --3-[(acetyloxy)--. Column 19, line 52 ...P-(N,N-... should read --p-(N,N----. Table V, 5th listing, 3rd Column ...phenyl]lactic... should read-phenyl]lactic acid--; 8th listing, 3rd Column ...butyric aci... should read --butyric acid--; 9th listing, 2nd Column ...monothiocarbamate acid... should read --monothiocarbamate--; 9th listing, 3rd Column ...phen-... should read --phenoxyacetic acid--; 12th listing, 3rd Column ...aci... should read --acid--; 24th listing, 3rd Column ...glycne... should read-glycine--; 29th listing, 2nd Column ...di-n-propyldithio-... should read --di-n-propyldithiocarbamate--; 29th listing, 3rd Column [p-N,N-di-n-propyldithio-... should read --[p-N,N-di-n-propyldithiocarbamate-methyl)anilino]butyric acid--; 32nd listing, 3rd Column ...glycne... should read --glycine--. Table VI, 9th listing, 2nd Column ...phenyl]ace-azabicyclo... should read --phenyl]-acetyl]amino]-8-oxo-5-thia-1-azabicyclo--. Table IX, 6th listing, 2nd Column ...carboxylic... should read --carboxylic acid--; 7th listing, 1st Column ...aicd... should read --acid--; 10th listing, 1st Column ...aicd... should read --acid--. Column 37, last paragraph ...following Table X... should read --following Table X gives the corresponding cephalosporin product listed in Table X--. Table X, 3rd listing, 1st Column

UNITED STATES PATENT OFFICE
CERTIFICATE OF CORRECTION

PATENT NO. : 4,031,083
DATED : February 16, 1978
INVENTOR(S) : F. Haviv, A. Patchornik and J. Altman It is certified that error appears in the above-identified patent and that said Letters Patent are hereby corrected as shown below:

...aicd... should read --acid--; 4th listing, 2nd Column
...aicd... should read --acid--; 4th listing, 3rd Column
...7-methoxyl... should read --7-methoxy--; 6th listing, 3rd Column ...thia-azabicyclo... should read --thia-1-azabicyclo--; 7th listing, 3rd Column ...-2-amino-acetyl]-8-... should read ---2-aminoacetyl amino]-8---. Table XI, 6th listing, 3rd Column ...0010 50... should read --thiocarbamatemethyl)-thienyl]--.

Signed and Sealed this

*Twenty-third* Day of *May 1978*

[SEAL]

*Attest:*

RUTH C. MASON
*Attesting Officer*

LUTRELLE F. PARKER
*Acting Commissioner of Patents and Trademarks*